(12) United States Patent
Van Den Berg et al.

(10) Patent No.: US 6,602,682 B1
(45) Date of Patent: Aug. 5, 2003

(54) KLUYVEROMYCES AS A HOST STRAIN

(75) Inventors: Johan Abel Van Den Berg, Reeuwijk (NL); Albert Johannes Joseph Van Ooyen, Voorburg (NL); Krijn Rietveld, Vlaardingen (NL); Cornelis P. Hollenberg, Dusseldorf (DE); Sunil Das, Dusseldorf (DE); Albert De Leeuw, Pijnacker (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 07/711,556

(22) Filed: May 29, 1991

Related U.S. Application Data

(63) Continuation of application No. 07/480,102, filed on Feb. 14, 1990, now abandoned, which is a continuation of application No. 07/300,608, filed on Jan. 23, 1989, now abandoned, which is a continuation of application No. 07/078,539, filed on Jul. 28, 1987, now Pat. No. 4,943,529, which is a continuation of application No. 06/572,414, filed on Jan. 19, 1984, now Pat. No. 4,859,596.

(30) Foreign Application Priority Data

May 19, 1982 (NL) .............................. 82/02091

(51) Int. Cl.$^7$ .......................... C12N 15/00; C12N 5/00; C12P 21/00; C07H 15/12
(52) U.S. Cl. ................ 435/69.1; 435/91.1; 435/255.01; 435/320.01
(58) Field of Search ............................. 435/69.1, 71.1, 435/91.1, 317.1, 122.3, 255.1, 256, 320.1, 68

(56) References Cited

U.S. PATENT DOCUMENTS

| | | | |
|---|---|---|---|
| 4,546,082 A | * 10/1985 | Kurjan .................... | 435/172.3 |
| 4,657,857 A | 4/1987 | Edens et al. ................ | 435/69.1 |
| 4,775,622 A | * 10/1988 | Hitzeman ..................... | 435/68 |

FOREIGN PATENT DOCUMENTS

| EP | 0096430 | * 12/1983 | .......... C12N/15/00 |
|---|---|---|---|
| EP | A1 096 910 | 12/1983 | |
| EP | A1 0 116 201 | 8/1984 | |
| EP | A2 241 435 | 10/1987 | |

OTHER PUBLICATIONS

Tubb, R. Chemical Abstracts vol. 106, No. 79656g , 1987.*

Bennetzen, J. et al., *J. Biol. Chem.*, vol. 257, No. 6, p. 3018–25, 1982.*

Innis, M. et al., *Science*, vol. 228, p. 21–26, 1985.*

Lemontt, J. et al., Chemical Abstracts, vol. 104, No. 1431160, 1986.*

Dal, S. et al., *Current Genetics*, p. 123–128, 1982.*

* cited by examiner

*Primary Examiner*—Gary Kunz
(74) *Attorney, Agent, or Firm*—McDonnell Boehnen Hulbert & Berghoff

(57) ABSTRACT

Kluyveromyces hosts and DNA expression cassettes for use in Kluyveromyces are provided for transcription of endogenous and/or exogenous DNA, and production of peptides, for enhancing production of an endogenous product, or producing an exogenous product. The Kluyveromyces hosts find particular use for secretion of a desired peptide product, where signal sequences may be native to the peptide or provided from endogenous or exogenous signal sequences, including synthetic sequences, functional in Kluyveromyces. A transformation procedure is provided for efficiently transforming Kluyveromyces.

7 Claims, 28 Drawing Sheets

FIGURE 3

Oligonucleotides used for the synthesis of the amyloglucosidase leader and protein sequence of the putative leader.

A

(1) 5' TCGATATGTCTTTCAGATCCCTACTAGCTCTATCCG 3'

(2) 5' GTCTAGTTTGTACTGGTCTAGCTAACGTTATCTCCAAGAGAG 3'

(3) 5' TCGACTCTCTTGGAGATAACGTTAGCTAGACCAGTACAAACTAGACCGGATAG AGCTAGTAGGGATCTGAAAGACATA 3'

B

Met Ser Phe Arg Ser Leu Leu Ala Leu Ser Gly Leu Val Cys Thr Gly Leu Ala Asn Val Ile Ser Lys Arg

FIGURE 4

Oligonucleotides used for the synthesis of the synthetic leader and protein sequence of the putative leader.

A
(1) 5' TCGAATCTAATCTAAGTTTTAATTACAAAATGGCT 3'
(2) 5' TTCAGATCCTTGTTGGCTTTGTCCGGTTTGTCCTGTGGTGCTTTGGCTGCTCAAG 3'
(3) 5' TCGACTTGAGCAGCCAAAGCACCACAGGACAAACC 3'
(4) 5' GGACAAAGCCAACAAGGATCTGAAAGCCATTTTGTAATTAAAACTTAGATTAGAT 3'

B
Met Ala Phe Arg Ser Leu Leu Ala Leu Ser Gly Leu
Ser Cys Gly Ala Leu Ala Ala Glu

Immunoblot showing prochymosin secreted by the AG leader sequence. The experiment was performed as described in Example 5B. The supernatant from a culture of K. lactis transformed with pGB905 was than treated with acid (pH 2) for 2 hours or 6 hours.

Lane 1: no treatment;
        Lane 2: 2 hour treatment;
        Lane 3: 6 hour treatment.

```
  1 GGATCCCCAGCTTAGTTCATAGGTCCATTCTCTTAGCGCAACTACAGAGAACAGGGGCACAA
    CCTAGGGGTCGAATCAAGTATCCAGGTAAGAGAATCGCGTTGATGTCTCTTGTCCCCGTGTT
    ^
    1 BAMHI,

63 ACAGGCAAAAAACGGGCACAACCTCAATGGAGTGATGCAACCTGCCTGGAGTAAATGATG
    TGTCCGTTTTTTGCCCGTGTTGGAGTTACCTCACTACGTTGGACGGACCTCATTTACTAC

123 ACACAAGGCAATTGACCCACGCATGTATCTATCTCATTTTCTTACACCTTCTATTACCTT
    TGTGTTCCGTTAACTGGGTGCGTACATAGATAGAGTAAAAGAATGTGGAAGATAATGGAA

183 CTGCTCTCTCTGATTTGGAAAAAGCTGAAAAAAAAGGTTGAAACCAGTTCCCTGAAATTA
    GACGAGAGAGACTAAACCTTTTTCGACTTTTTTTTCCAACTTTGGTCAAGGGACTTTAAT
                                                              ^
    236 XMNI,

243 TTCCCCTACTTGACTAATAAGTATATAAAGACGGTAGGTATTGATTGTAATTCTGTAAAT
    AAGGGGATGAACTGATTATTCATATATTTCTGCCATCCATAACTAACATTAAGACATTTA

303 CTATTTCTTAAACTTCTTAAATTCTACTTTTATAGTTAGTCTTTTTTTTAGTTTTAAAAC
    GATAAAGAATTTGAAGAATTTAAGATGAAAATATCAATCAGAAAAAAATCAAAATTTTG
                                                             ^
    355 AHA3,

MetArgPheProSerIle
363 ACCAAGAACTTAGTTTCGAATAAACACACATAAACAAACACCATGAGATTTCCTTCAATT
    TGGTTCTTGAATCAAAGCTTATTTGTGTGTATTTGTTTGTGGTACTCTAAAGGAAGTTAA
                       ^
    377 ASU2,

PheThrAlaValLeuPheAlaAlaSerSerAlaLeuAlaAlaProValAsnThrThrThr
423 TTTACTGCAGTTTTATTCGCAGCATCCTCCGCATTAGCTGCTCCAGTCAACACTACAACA
    AAATGACGTCAAAATAAGCGTCGTAGGAGGCGTAATCGACGAGGTCAGTTGTGATGTTGT
        ^
    427 PSTI,

GluAspGluThrAlaGlnIleProAlaGluAlaValIleGlyTyrLeuAspLeuGluGly
483 GAAGATGAAACGGCACAAATTCCGGCTGAAGCTGTCATCGGTTACTTAGATTTAGAAGGG
    CTTCTACTTTGCCGTGTTTAAGGCCGACTTCGACAGTAGCCAATGAATCTAAATCTTCCC

AspPheAspValAlaValLeuProPheSerAsnSerThrAsnAsnGlyLeuLeuPheIle
543 GATTTCGATGTTGCTGTTTTGCCATTTTCCAACAGCACAAATAACGGGTTATTGTTTATA
    CTAAAGCTACAACGACAAAACGGTAAAAGGTTGTCGTGTTTATTGCCCAATAACAAATAT

AsnThrThrIleAlaSerIleAlaAlaLysGluGluGlyValSerLeuAspLysArgAla
603 AATACTACTATTGCCAGCATTGCTGCTAAAGAAGAAGGGGTATCTCTAGATAAAAGAGCT
    TTATGATGATAACGGTCGTAACGACGATTTCTTCTTCCCCATAGAGATCTATTTTCTCGA
                                                           ^
    647 XBAI,

GAP/Alpha-Factor/Prochymosin Insert in pDM100PC
```

```
       GluIleThrArgIleProLeuTyrLysGlyLysSerLeuArgLysAlaLeuLysGluHis
 663   GAGATCACCAGGATCCCTCTGTACAAAGGCAAGTCTCTGAGGAAGGCGCTGAAGGAGCAT
       CTCTAGTGGTCCTAGGGAGACATGTTTCCGTTCAGAGACTCCTTCCGCGACTTCCTCGTA

673 BAMHI,

GlyLeuLeuGluAspPheLeuGlnLysGlnGlnTyrGlyIleSerSerLysTyrSerGly
 723   GGGCTTCTGGAGGACTTCCTGCAGAAACAGCAGTATGGCATCAGCAGCAAGTACTCCGGC
       CCCGAAGACCTCCTGAAGGACGTCTTTGTCGTCATACCGTAGTCGTCGTTCATGAGGCCG

741 PSTI, 772 SCAI,

PheGlyGluValAlaSerValProLeuThrAsnTyrProAspSerGlnTyrPheGlyLys
 783   TTCGGGGAGGTGGCCAGCGTCCCCCTGACCAACTACCCGGACAGTCAGTACTTTGGAAG
       AAGCCCCTCCACCGGTCGCAGGGGGACTGGTTGATGGGCCTGTCAGTCATGAAACCCTTC

793 BALI, 829 SCAI, 841 BGL2,

IleTyrLeuGlyThrProProGlnGluPheThrValLeuPheAspThrGlySerSerAsp
 843   ATCTACCTCGGGACCCCGCCCCAGGAGTTCACCGTGCTGTTTGACACTGGCTCCTCTGAC
       TAGATGGAGCCCTGGGGCGGGGTCCTCAAGTGGCACGACAAACTGTGACCGAGGAGACTG

PheTrpValProSerMetTyrCysLysSerAsnAlaCysLysAsnHisGlnArgPheAsp
 903   TTCTGGGTACCCTCTATGTACTGCAAGAGCAATGCCTGCAAAAACCACCAGCGCTTCGAC
       AAGACCCATGGGAGATACATGACGTTCTCGTTACGGACGTTTTGGTGGTCGCGAAGCTG

908 KPNI,

ProArgLysSerSerThrPheGlnAsnLeuGlyLysProLeuSerIleHisTyrGlyThr
 963   CCGAGAAAGTCGTCCACCTTCCAGAACCTGGGCAAGCCCCTGTCTATCCACTACGGGACA
       GGCTCTTTCAGCAGGTGGAAGGTCTTGGACCCGTTCGGGGACAGATAGGTGATGCCCTGT

983 PFLM1, 984 ALWN1,

GlySerMetGlnGlyIleLeuGlyTyrAspThrValThrValSerAsnIleValAspIle
1023   GGCAGCATGCAGGGCATCCTGGGCTATGACACCGTCACTGTCTCCAACATTGTGGACATC
       CCGTCGTACGTCCCGTAGGACCCGATACTGTGGCAGTGACAGAGGTTGTAACACCTGTAG

1027 SPHI, 1050 TTH3I, 1066 BSTXI,

GlnGlnThrValGlyLeuSerThrAspGluProGlyAspValPheThrTyrAlaGluPhe
1083   CAGCAGACAGTAGGCCTGAGCACCGACGAGCCCGGGGACGTCTTCACCTATGCCGAATTC
       GTCGTCTGTCATCCGGACTCGTGGCTGCTCGGGCCCCTGCAGAAGTGGATACGGCTTAAG

1094 STUI, 1113 SMAI XMAI, 1119 AAT2, 1137 ECORI,

AspGlyIleLeuGlyMetAlaTyrProSerLeuAlaSerGluTyrSerThrSerValPhe
1143   GACGGGATCCTGGGGATGGCCTACCCCTCGCTCGCCTCAGAGTACTCGACATCCGTGTTT
       CTGCCCTAGGACCCCTACCGGATGGGGAGCGAGCGGAGTCTCATGAGCTGTAGGCACAAA

1147 BAMHI, 1183 SCAI,
```

```
             AspAsnMetMetAsnArgHisLeuValAlaGlnAspLeuPheSerValTyrMetAspArg
    1203     GACAACATGATGAACAGGCACCTGGTGGCCCAAGACCTGTTCTCGGTTTACATGGACAGG
             CTGTTGTACTACTTGTCCGTGGACCACCGGGTTCTGGACAAGAGCCAAATGTACCTGTCC

1221 DRA3,

AsnGlyGlnGluSerMetLeuThrLeuGlyProIleAspProSerTyrTyrThrGlySer
    1263     AATGGCCAGGAGAGCATGCTCACGCTGGGGCCCATCGACCCGTCCTACTACACAGGGTCC
             TTACCGGTCCTCTCGTACGAGTGCGACCCCGGGTAGCTGGGCAGGATGATGTGTCCCAGG

1265 BALI, 1276 SPHI, 1290 APAI,

LeuHisTrpValProValThrValGlnGlnTyrTrpGlnPheThrValAspSerValThr
    1323     CTGCATTGGGTGCCCGTGACAGTGCAGCAGTACTGGCAGTTCACTGTGGACAGTGTCACC
             GACGTAACCCACGGGCACTGTCACGTCGTCATGACCGTCAAGTGACACCTGTCACAGTGG

1351 SCAI, 1371 TTH3I, 1380 HGIE2,

IleSerGlyValValValProCysGluGlyGlyCysGlnAlaIleLeuAspThrGlyThr
    1383     ATCAGCGGTGTGGTTGTGCCCTGTGAGGGTGGCTGTCAGGCCATCCTGGACACGGGCACC
             TAGTCGCCACACCAACACGGGACACTCCCACCGACAGTCCGGTAGGACCTGTGCCCGTGG

SerLysLeuValGlyProSerSerAspIleLeuAsnIleGlnGlnProIleGlyAlaThr
    1443     TCCAAGCTGGTCGGGCCCAGCAGCGACATCCTCAACATCCAGCAGCCCATTGGAGCCACA
             AGGTTCGACCAGCCCGGGTCGTCGCTGTAGGAGTTGTAGGTCGTCGGGTAACCTCGGTGT

1455 APAI,

GlnAsnGlnTyrGlyAspPheAspIleAspCysAspAsnLeuSerTyrMetProThrVal
    1503     CAGAACCAGTACGGTGATTTTGACATCGACTGCGACAACCTGAGCTACATGCCCACTGTG
             GTCTTGGTCATGCCACTAAAACTGTAGCTGACGCTGTTGGACTCGATGTACGGGTGACAC

ValPheGluIleAsnGlyLysIleTyrProLeuThrProSerAlaTyrThrSerGlnAsp
    1563     GTCTTTGAGATCAATGGCAAAATCTACCCACTGACCCCCTCCGCCTATACCAGCCAGGAC
             CAGAAACTCTAGTTACCGTTTTAGATGGGTGACTGGGGGAGGCGGATATGGTCGGTCCTG

GlnGlyPheCysThrSerGlyPheGlnSerGluAsnHisSerGlnLysTrpIleLeuGly
    1623     CAGGGCTTCTGTACCAGTGGCTTCCAGAGTGAAAATCATTCCCAGAAATGGATCCTGGGG
             GTCCCGAAGACATGGTCACCGAAGGTCTCACTTTTAGTAAGGGTCTTTACCTAGGACCCC

1672 BAMHI,

AspValPheIleArgGluTyrTyrSerValPheAspArgProAsnAsnLeuValGlyLeu
    1683     GATGTTTTCATCCGAGAGTATTACAGCGTCTTTGACAGGCCCAACAACCTCGTGGGGCTG
             CTACAAAAGTAGGCTCTCATAATGTCGCAGAAACTGTCCGGGTTGTTGGAGCACCCCGAC

1741 BALI,

AlaLysAlaIleOP
    1743     GCCAAAGCCATCTGATCTCGACTTGGTTGAACACGTTGCCAAGGCTTAAGTGAATTTACT
             CGGTTTCGGTAGACTAGAGCTGAACCAACTTGTGCAACGGTTCCGAATTCACTTAAATGA

1787 AFL2, 1802 AHA3,
```

```
1803   TTAAAGTCTTGCATTTAAATAAATTTTCTTTTTATAGCTTTATGACTTAGTTTCAATTTA
       AATTTCAGAACGTAAATTTATTTAAAAGAAAAATATCGAAATACTGAATCAAAGTTAAAT

1816 AHA3,

1863   TATACTATTTTAATGACATTTTCGATTCATTGATTGAAAGCTTTGTGTTTTTTCTTGATG
       ATATGATAAAATTACTGTAAAAGCTAAGTAACTAACTTTCGAAACACAAAAAAGAACTAC

1900 HIND3,

1923   CGCTATTGCATTGTTCTTGTCTTTTTCGCCACATGTAATATCTGTAGTAGATACCTGATA
       GCGATAACGTAACAAGAACAGAAAAAGCGGTGTACATTATAGACATCATCTATGGACTAT

1983   CATTGTGGATGCTGAGTGAAATTTTAGTTAATAATGGAGGCGCTCTTAATAATTTTGGGG
       GTAACACCTACGACTCACTTTAAAATCAATTATTACCTCCGCGAGAATTATTAAAACCCC

2043   ATATTGGCTTTTTTTTTTAAAGTTTACAAATGAATTTTTTCCGCCAGGATAACGATTCTG
       TATAACCGAAAAAAAAAATTTCAAATGTTTACTTAAAAAAGGCGGTCCTATTGCTAAGAC

2058 AHA3, 2074 XMNI,

2103   AAGTTACTCTTAGCGTTCCTATCGGTACAGCCATCAAATCATGCCTATAAATCATGCCTA
       TTCAATGAGAATCGCAAGGATAGCCATGTCGGTAGTTTAGTACGGATATTTAGTACGGAT

2163   TATTTGCGTGCAGTCAGTATCATCTACATGAAAAAAACTCCCGCAATTTCTTATAGAATA
       ATAAACGCACGTCAGTCATAGTAGATGTACTTTTTTTGAGGGCGTTAAAGAATATCTTAT

2223   CGTTGAAAATTAAATGTACGCGCCAAGATAAGATAACATATATCTAGCTAGATGCAGTAA
       GCAACTTTTAATTTACATGCGCGGTTCTATTCTATTGTATATAGATCGATCTACGTCATT

2283   TATACACAGATTCCCGCGGACGTGGGAAGGAAAAAATTAGATAACAAAATCTGAGTGATA
       ATATGTGTCTAAGGGCGCCTGCACCCTTCCTTTTTAATCTATTGTTTTAGACTCACTAT

2296 SAC2,

2343   TGGAAATTCCGCTGTATAGCTCATATCTTTCCCTTCAACACCAGAAATGTAAAAATCTTG
       ACCTTTAAGGCGACATATCGAGTATAGAAAGGGAAGTTGTGGTCTTTACATTTTTAGAAC

2403   TTACGAAGGATCTTTTTGCTAATGTTTCTCGCTCAATCCTCATTTCTTCCCTACGAAGAG
       AATGCTTCCTAGAAAAACGATTACAAAGAGCGAGTTAGGAGTAAAGAAGGGATGCTTCTC

2463   TCAAATCTACTTGTTTTCTGCCGGTATCAAGATCCATATCTTCTAGTTTCACCATCAAAG
       AGTTTAGATGAACAAAAGACGGCCATAGTTCTAGGTATAGAAGATCAAAGTGGTAGTTTC

2523   TCCAATTTCTAGTATACAGTTTATGTCCCAACGTAACAGACAATCAAAATTGGAAAGGAT
       AGGTTAAAGATCATATGTCAAATACAGGGTTGCATTGTCTGTTAGTTTTAACCTTTCCTA

2534 SNAI XCA1,

2583   AAGTATCCTTCAAAGAATGATTCTGCGCTGGCTCCTGAACCGCCTAATGGGAACAGAGAA
       TTCATAGGAAGTTTCTTACTAAGACGCGACCGAGGACTTGGCGGATTACCCTTGTCTCTT
```

2643 GTCCAAAACGATGCTATAAGAACCAGAAATAAAACGATAAAACCATACCAGGATCGGTCG
CAGGTTTTGCTACGATATTCTTGGTCTTTATTTTGCTATTTTGGTATGGTCCTAGCCAGC

2689 HGIE2, 2699 SALI,

2703 ACTTTGTTCCCACTGTACTTTTAGCTCGTACAAAATACAATATACTTTTCATTTCTCCGT
TGAAACAAGGGTGACATGAAAATCGAGCATGTTTTATGTTATATGAAAAGTAAAGAGGCA

2763 AAACAACATGTTTTCCCATGTAATATCCTTTTCTATTTTTCGTTCCGTTACCAACTTTAC
TTTGTTGTACAAAAGGGTACATTATAGGAAAAGATAAAAAGCAAGGCAATGGTTGAAATG

2823 ACATACTTTATATAGCTATTCACTTCTATACACTAAAAAACTAAGACAATTTTAATTTTG
TGTATGAAATATATCGATAAGTGAAGATATGTGATTTTTTGATTCTGTTAAAATTAAAAC

2883 CTGCCTGCCATATTTCAATTTGTTATAAATTCCTATAATTTATCCTATTAGTAGCTAAAA
GACGGACGGTATAAAGTTAAACAATATTTAAGGATATTAAATAGGATAATCATCGATTTT

2943 AAAGATGAATGTGAATCGAATCCTAAGAGAATTCGGATCC
TTTCTACTTACACTTAGCTTAGGATTCTCTTAAGCCTAGG

2971 ECORI, 2977 BAMHI,

```
            Trp Ser Trp Ile Thr Leu
            TGG QZV TGG ATL ACN YTI
```

Code for ambiguous bases:

```
Q:   A or T          L:   A,T, or C
R:   A or G          N:   any base
S:   A or C          V:   T or C if preceded by AG; else any base
Y:   T or C          I:   A or G if preceded by TT; else any base
Z:   C or G          P:   A or G if preceded by AG; else any base
```

---

```
           3'                     5'
POOL #1     ACC AGG ACC TAG TGG GA
                  A       A   A A
                  T       T   T
                  C           C

3'                     5'
POOL #2     ACC TCG ACC TAG TGG GA
                  A       A   A A
                          T   T
                              C
```

FIGURE 8

```
  1  CTGCAGTTTGTGAATCGTAAGACAGTGACATTTTTAGAGGTTGTTATCTGTTTAAGACGA
     GACGTCAAACACTTAGCATTCTGTCACTGTAAAAATCTCCAACAATAGACAAATTCTGCT

61  AATGGTTTGCTGTTCAAGCTCACTGGGTGATCGGATTTCGGGAAAATTCATATATAAAGG
     TTACCAAACGACAAGTTCGAGTGACCCACTAGCCTAAAGCCCTTTTAAGTATATATTTCC

1 PST1, 81 DRA3,

121  ACCCTTGATTGATAGGATGTTATGGTATTGTTCTAAGTTTGTTTCAATAGTAATTTCAAT
     TGGGAACTAACTATCCTACAATACCATAACAAGATTCAAACAAAGTTATCATTAAAGTTA

181  ATAGTATATTAGAACAAGCAAACCAGAGCATCTAAAGCCCAACTCGTCTGATCTTTTTCT
     TATCATATAATCTTGTTCGTTTGGTCTCGTAGATTTCGGGTTGAGCAGACTAGAAAAAGA

241  GTCTTTATTATCCTGAACTTCACCTTAATCTAAATTATACAAACCCAACTATCCAATTTG
     CAGAAATAATAGGACTTGAAGTGGAATTAGATTTAATATGTTTGGGTTGATAGGTTAAAC

MetLysPheSerThrIleLeuAlaAlaSerThrAlaLeuIleSer
301  AACTATCCAATATTATGAAATTCTCTACTATATTAGCCGCATCTACTGCTTTAATTTCC
     TTGATAGGTTATAATACTTTAAGAGATGATATAATCGGCGTAGATGACGAAATTAAAGG

309 SSP1,

ValValMetAlaAlaProValSerThrGluThrAspIleAspAspLeuProIleSerVal
361  GTTGTTATGGCTGCTCCAGTTTCTACCGAAACTGACATCGACGATCTTCCAATTTCGGTT
     CAACAATACCGACGAGGTCAAAGATGGCTTTGACTGTAGCTGCTAGAAGGTTAAAGCCAA

ProGluGluAlaLeuIleGlyPheIleAspLeuThrGlyAspGluValSerLeuLeuPro
421  CCAGAAGAAGCCTTGATTGGATTCATTGACTTAACCGGGGATGAAGTTTCCTTGTTGCCT
     GGTCTTCTTCGGAACTAACCTAAGTAACTGAATTGGCCCCTACTTCAAAGGAACAACGGA

ValAsnAsnGlyThrHisThrGlyIleLeuPheLeuAsnThrThrIleAlaGluAlaAla
481  GTTAATAACGGAACCCACACTGGTATTCTATTCTTAAACACCACCATCGCTGAAGCTGCT
     CAATTATTGCCTTGGGTGTGACCATAAGATAAGAATTTGTGGTGGTAGCGACTTCGACGA

PheAlaAspLysAspAspLeuLysLysArgGluAlaAspAlaSerProTrpSerTrpIle
541  TTCGCTGACAAGGATGATTTGAAGAAAAGAGAAGCCGATGCTTCCCCATGGAGTTGGATT
     AAGCGACTGTTCCTACTAAACTTCTTTTCTCTTCGGCTACGAAGGGGTACCTCAACCTAA

585 BSTXI NCO1,

ThrLeuArgProGlyGlnProIlePheLysArgGluAlaAsnAlaAspAlaAsnAlaGluAla
601  ACTCTAAGACCTGGTCAACCAATCTTTAAAAGAGAAGCCAACGCTGACGCTAATGCTGAAGCA
     TGAGATTCTGGACCAGTTGGTTAGAAATTTTCTCTTCGGTTGCGACTGCGATTACGACTTCGT

607 TTH3I, 624 AHA3,
```

```
         SerProTrpSerTrpIleThrLeuArgProGlyGlnProIlePheLysArgGluAlaAsn
663      TCCCCATGGAGCTGGATTACTCTAAGACCTGGTCAACCGATCTTTAAGAGAGAGGCTAAT
         AGGGGTACCTCGACCTAATGAGATTCTGGACCAGTTGGCTAGAAATTCTCTCTCCGATTA

666 BSTXI, NCOI, 688 TTH3I

AlaAspAlaAsnAlaAspAlaSerProTrpSerTrpIleThrLeuArgProGlyGlnPro
723      GCTGATGCCAATGCAGATGCCTCCCCATGGAGCTGGATCACTCTAAGACCTGGTCAACCA
         CGACTACGGTTACGTCTACGGAGGGGTACCTCGACCTAGTGAGATTCTGGACCAGTTGGT

747 BSTXI, NCOI, 769 TTH3I

IlePheLysArgGluAlaAsnProGluAlaGluAlaAspAlaLysProSerAlaTrpSer
783      ATCTTTAAAAGAGAAGCCAACCCTGAGGCCGAGGCTGATGCCAAACCTAGTGCTTGGAGT
         TAGAAATTTTCTCTTCGGTTGGGACTCCGGCTCCGACTACGGTTTGGATCACGAACCTCA

786 AHA3, 804 MST2

TrpIleThrLeuArgProGlyGlnProIlePheOP
843      TGGATTACATTAAGACCTGGCCAACCAATTTTCTGAATTAGAAGGAAATTGACTTTTTGA
         ACCTAATGTAATTCTGGACCGGTTGGTTAAAAGACTTAATCTTCCTTTAACTGAAAAACT

860 BALI

903      CTCGTTTTCCAATGCGTCTATCTAATTTCTTCCAAAAGACAATACCCATCTTCCTTATAC
         GAGCAAAAGGTTACGCAGATAGATTAAAGAAGGTTTTCTGTTATGGGTAGAAGGAATATG

963      TTTTTTTATTTATCCAAACGAATTC
         AAAAAAATAAATAGGTTTGCTTAAG

982 ECORI
```

```
            <---α-Factor Leader--><----(Spacer)-Prochymosin------------->
pAB309,    AspAspLeuLysLysArgGluAlaAspAlaSerHisHisMetAlaGluIleThrArgIle
pAB312     GATGATTTGAAGAAAAGAGAAGCCGATGCTTCCCATCATATGGCTGAGATCACCAGGATC
           CTACTAAACTTCTTTTCTCTTCGGCTACGAAGGGTAGTATACCGACTCTAGTGGTCCTAG AspAspLeuLysLysArgAlaGluIleThrArgIleProLeuTyrLysGly
pAB313     GATGATTTGAAGAAAAGAGCTGAGATCACCAGGATCCCTCTGTACAAAGGC
           CTACTAAACTTCTTTTCTCGACTCTAGTGGTCCTAGGGAGACATGTTTCCG AspAspLeuLysLysArgAlaGluIleThrArgIleProLeuTyrLysGly
pAB314     GATGATTTGAAGAAGCGCGCTGAGATCACCAGGATCCCTCTGTACAAAGGC
           CTACTAAACTTCTTCGCGCGACTCTAGTGGTCCTAGGGAGACATGTTTCCG
                          BssHII
```

FIGURE 11  Sequences Around the Junctions in Alpha-Factor Leader/Prochymosin Fusions pAB309 BamHI/SalI Insert in pUC18

```
  1  GGATCCCCAGCTTAGTTCATAGGTCCATTCTCTTAGCGCAACTACAGAGAACAGGGGCAC
     CCTAGGGGTCGAATCAAGTATCCAGGTAAGAGAATCGCGTTGATGTCTCTTGTCCCCGTG
     ^
  1 BAMHI,

61  AAACAGGCAAAAAACGGGCACAACCTCAATGGAGTGATGCAACCTGCCTGGAGTAAATGA
     TTTGTCCGTTTTTTGCCCGTGTTGGAGTTACCTCACTACGTTGGACGGACCTCATTTACT

121  TGACACAAGGCAATTGACCCACGCATGTATCTATCTCATTTTCTTACACCTTCTATTACC
     ACTGTGTTCCGTTAACTGGGTGCGTACATAGATAGAGTAAAAGAATGTGGAAGATAATGG

181  TTCTGCTCTCTCTGATTTGGAAAAAGCTGAAAAAAAGGTTGAAACCAGTTCCCTGAAAT
     AAGACGAGAGAGACTAAACCTTTTCGACTTTTTTTCCAACTTTGGTCAAGGGACTTTA
                                                            ^
 236 XMNI,

241  TATTCCCCTACTTGACTAATAAGTATATAAAGACGGTAGGTATTGATTGTAATTCTGTAA
     ATAAGGGGATGAACTGATTATTCATATATTTCTGCCATCCATAACTAACATTAAGACATT

301  ATCTATTTCTTAAACTTCTTAAATTCTACTTTTATAGTTAGTCTTTTTTTTAGTTTTAAA
     TAGATAAAGAATTTGAAGAATTTAAGATGAAAATATCAATCAGAAAAAAAATCAAAATTT
                                                              ^
 355 AHA3,

MetLysPheSer
361  ACACCAAGAACTTAGTTTCGAATAAACACACATAAACAGATCTTCATTATGAAATTCTCT
     TGTGGTTCTTGAATCAAAGCTTATTTGTGTGTATTTGTCTAGAAGTAATACTTTAAGAGA
                   ^                              ^
 377 ASU2, 398 BGL2,

ThrIleLeuAlaAlaSerThrAlaLeuIleSerValValMetAlaAlaProValSerThr
421  ACTATATTAGCCGCATCTACTGCTTTAATTTCCGTTGTTATGGCTGCTCCAGTTTCTACC
     TGATATAATCGGCGTAGATGACGAAATTAAAGGCAACAATACCGACGAGGTCAAAGATGG

GluThrAspIleAspAspLeuProIleSerValProGluGluAlaLeuIleGlyPheIle
481  GAAACTGACATCGACGATCTTCCAATTTCGGTTCCAGAAGAAGCCTTGATTGGATTCATT
     CTTTGACTGTAGCTGCTAGAAGGTTAAAGCCAAGGTCTTCTTCGGAACTAACCTAAGTAA

AspLeuThrGlyAspGluValSerLeuLeuProValAsnAsnGlyThrHisThrGlyIle
541  GACTTAACCGGGGATGAAGTTTCCTTGTTGCCTGTTAATAACGGAACCCACACTGGTATT
     CTGAATTGGCCCCTACTTCAAAGGAACAACGGACAATTATTGCCTTGGGTGTGACCATAA
                                                          ^
 586 HGIE2,
```

```
        LeuPheLeuAsnThrThrIleAlaGluAlaAlaPheAlaAspLysAspAspLeuLysLys
601     CTATTCTTAAACACCACCATCGCTGAAGCTGCTTTCGCTGACAAGGATGATTTGAAGAAA
        GATAAGAATTTGTGGTGGTAGCGACTTCGACGAAAGCGACTGTTCCTACTAAACTTCTTT

ArgGluAlaAspAlaSerHisHisMetAlaGluIleThrArgIleProLeuTyrLysGly
661     AGAGAAGCCGATGCTTCCCATCATATGGCTGAGATCACCAGGATCCCTCTGTACAAAGGC
        TCTCTTCGGCTACGAAGGGTAGTATACCGACTCTAGTGGTCCTAGGGAGACATGTTTCCG

682 NDEI, 701 BAMHI,

LysSerLeuArgLysAlaLeuLysGluHisGlyLeuLeuGluAspPheLeuGlnLysGln
721     AAGTCTCTGAGGAAGGCGCTGAAGGAGCATGGGCTTCTGGAGGACTTCCTGCAGAAACAG
        TTCAGAGACTCCTTCCGCGACTTCCTCGTACCCGAAGACCTCCTGAAGGACGTCTTTGTC

769 PSTI,

GlnTyrGlyIleSerSerLysTyrSerGlyPheGlyGluValAlaSerValProLeuThr
781     CAGTATGGCATCAGCAGCAAGTACTCCGGCTTCGGGGAGGTGGCCAGCGTCCCCCTGACC
        GTCATACCGTAGTCGTCGTTCATGAGGCCGAAGCCCCTCCACCGGTCGCAGGGGGACTGG

800 SCAI, 821 BALI, 839 BSTXI,

AsnTyrLeuAspSerGlnTyrPheGlyLysIleTyrLeuGlyThrProProGlnGluPhe
841     AACTACCTGGACAGTCAGTACTTTGGGAAGATCTACCTCGGGACCCCGCCCCAGGAGTTC
        TTGATGGACCTGTCAGTCATGAAACCCTTCTAGATGGAGCCCTGGGGCGGGGTCCTCAAG

857 SCAI, 869 BGL2,

ThrValLeuPheAspThrGlySerSerAspPheTrpValProSerIleTyrCysLysSer
901     ACCGTGCTGTTTGACACTGGCTCCTCTGACTTCTGGGTACCCTCTATCTACTGCAAGAGC
        TGGCACGACAAACTGTGACCGAGGAGACTGAAGACCCATGGGAGATAGATGACGTTCTCG

936 KPNI,

AsnAlaCysLysAsnHisGlnArgPheAspProArgLysSerSerThrPheGlnAsnLeu
961     AATGCCTGCAAAAACCACCAGCGCTTCGACCCGAGAAAGTCGTCCACCTTCCAGAACCTG
        TTACGGACGTTTTTGGTGGTCGCGAAGCTGGGCTCTTTCAGCAGGTGGAAGGTCTTGGAC

GlyLysProLeuSerIleHisTyrGlyThrGlySerMetGlnGlyIleLeuGlyTyrAsp
1021    GGCAAGCCCCTGTCTATCCACTACGGGACAGGCAGCATGCAGGGCATCCTGGGCTATGAC
        CCGTTCGGGGACAGATAGGTGATGCCCTGTCCGTCGTACGTCCCGTAGGACCCGATACTG

1055 SPHI, 1078 TTH3I,

ThrValThrValSerAsnIleValAspIleGlnGlnThrValGlyLeuSerThrGlnGlu
1081    ACCGTCACTGTCTCCAACATTGTGGACATCCAGCAGACAGTAGGCCTGAGCACCCAGGAG
        TGGCAGTGACAGAGGTTGTAACACCTGTAGGTCGTCTGTCATCCGGACTCGTGGGTCCTC

1094 BSTXI, 1122 STUI,
```

```
                ProGlyAspValPheThrTyrAlaGluPheAspGlyIleLeuGlyMetAlaTyrProSer
     1141       CCCGGGGACGTCTTCACCTATGCCGAATTCGACGGGATCCTGGGGATGGCCTACCCCTCG
                GGGCCCCTGCAGAAGTGGATACGGCTTAAGCTGCCCTAGGACCCCTACCGGATGGGGAGC

1141 SMAI, 1147 AAT2, 1165 ECORI, 1175 BAMHI,

LeuAlaSerGluTyrSerIleProValPheAspAsnMetMetAsnArgHisLeuValAla
     1201       CTCGCCTCAGAGTACTCGATACCCGTGTTTGACAACATGATGAACAGGCACCTGGTGGCC
                GAGCGGAGTCTCATGAGCTATGGGCACAAACTGTTGTACTACTTGTCCGTGGACCACCGG

1211 SCAI,

GlnAspLeuPheSerValTyrMetAspArgAsnGlyGlnGluSerMetLeuThrLeuGly
     1261       CAAGACCTGTTCTCGGTTTACATGGACAGGAATGGCCAGGAGAGCATGCTCACGCTGGGG
                GTTCTGGACAAGAGCCAAATGTACCTGTCCTTACCGGTCCTCTCGTACGAGTGCGACCCC

1293 BALI, 1304 SPHI,

AlaIleAspProSerTyrTyrThrGlySerLeuHisTrpValProValThrValGlnGln
     1321       GCCATCGACCCGTCCTACTACACAGGGTCCCTGCATTGGGTGCCCGTGACAGTGCAGCAG
                CGGTAGCTGGGCAGGATGATGTGTCCCAGGGACGTAACCCACGGGCACTGTCACGTCGTC

1379 SCAI,

TyrTrpGlnPheThrValAspSerValThrIleSerGlyValValValAlaCysGluGly
     1381       TACTGGCAGTTCACTGTGGACAGTGTCACCATCAGCGGTGTGGTTGTGGCCTGTGAGGGT
                ATGACCGTCAAGTGACACCTGTCACAGTGGTAGTCGCCACACCAACACCGGACACTCCCA

1399 TTH3I, 1408 HGIE2,

GlyCysGlnAlaIleLeuAspThrGlyThrSerLysLeuValGlyProSerSerAspIle
     1441       GGCTGTCAGGCCATCCTGGACACGGGCACCTCCAAGCTGGTCGGGCCCAGCAGCGACATC
                CCGACAGTCCGGTAGGACCTGTGCCCGTGGAGGTTCGACCAGCCCGGGTCGTCGCTGTAG

1483 APAI,

LeuAsnIleGlnGlnAlaIleGlyAlaThrGlnAsnGlnTyrGlyGluPheAspIleAsp
     1501       CTCAACATCCAGCAGGCCATTGGAGCCACACAGAACCAGTACGGTGAGTTTGACATCGAC
                GAGTTGTAGGTCGTCCGGTAACCTCGGTGTGTCTTGGTCATGCCACTCAAACTGTAGCTG

CysAspAsnLeuSerTyrMetProThrValValPheGluIleAsnGlyLysMetTyrPro
     1561       TGCGACAACCTGAGCTACATGCCCACTGTGGTCTTTGAGATCAATGGCAAAATGTACCCA
                ACGCTGTTGGACTCGATGTACGGGTGACACCAGAAACTCTAGTTACCGTTTTACATGGGT

LeuThrProSerAlaTyrThrSerGlnAspGlnGlyPheCysThrSerGlyPheGlnSer
     1621       CTGACCCCCTCCGCCTATACCAGCCAGGACCAGGGCTTCTGTACCAGTGGCTTCCAGAGT
                GACTGGGGGAGGCGGATATGGTCGGTCCTGGTCCCGAAGACATGGTCACCGAAGGTCTCA
```

```
                GluAsnHisSerGlnLysTrpIleLeuGlyAspValPheIleArgGluTyrTyrSerVal
      1681      GAAAATCATTCCCAGAAATGGATCCTGGGGGATGTTTTCATCCGAGAGTATTACAGCGTC
                CTTTTAGTAAGGGTCTTTACCTAGGACCCCCTACAAAAGTAGGCTCTCATAATGTCGCAG

1700 BAMHI,

PheAspArgAlaAsnAsnLeuValGlyLeuAlaLysAlaIleOP
      1741      TTTGACAGGGCCAACAACCTCGTGGGGCTGGCCAAAGCCATCTGATCTCGACTTGGTTGA
                AAACTGTCCCGGTTGTTGGAGCACCCCGACCGGTTTCGGTAGACTAGAGCTGAACCAACT

1769 BALI,

1801      ACACGTTGCCAAGGCTTAAGTGAATTTACTTTAAAGTCTTGCATTTAAATAAATTTTCTT
                TGTGCAACGGTTCCGAATTCACTTAAATGAAATTTCAGAACGTAAATTTATTTAAAAGAA

1815 AFL2,  1830 AHA3,  1844 AHA3,

1861      TTTATAGCTTTATGACTTAGTTTCAATTTATATACTATTTTAATGACATTTTCGATTCAT
                AAATATCGAAATACTGAATCAAAGTTAAATATATGATAAAATTACTGTAAAAGCTAAGTA

1921      TGATTGAAAGCTTTGTGTTTTTTCTTGATGCGCTATTGCATTGTTCTTGTCTTTTTCGCC
                ACTAACTTTCGAAACACAAAAAAGAACTACGCGATAACGTAACAAGAACAGAAAAAGCGG

1928 HIND3,

1981      ACATGTAATATCTGTAGTAGATACCTGATACATTGTGGATGCTGAGTGAAATTTTAGTTA
                TGTACATTATAGACATCATCTATGGACTATGTAACACCTACGACTCACTTTAAAATCAAT

2041      ATAATGGAGGCGCTCTTAATAATTTTGGGGATATTGGCTTTTTTTTTAAAGTTTACAAA
                TATTACCTCCGCGAGAATTATTAAAACCCCTATAACCGAAAAAAAAAATTTCAAATGTTT

2086 AHA3,

2101      TGAATTTTTTCCGCCAGGATAACGATTCTGAAGTTACTCTTAGCGTTCCTATCGGTACAG
                ACTTAAAAAAGGCGGTCCTATTGCTAAGACTTCAATGAGAATCGCAAGGATAGCCATGTC

2102 XMNI,

2161      CCATCAAATCATGCCTATAAATCATGCCTATATTTGCGTGCAGTCAGTATCATCTACATG
                GGTAGTTTAGTACGGATATTTAGTACGGATATAAACGCACGTCAGTCATAGTAGATGTAC

2221      AAAAAAACTCCCGCAATTTCTTATAGAATACGTTGAAAATTAAATGTACGCGCCAAGATA
                TTTTTTTGAGGGCGTTAAAGAATATCTTATGCAACTTTTAATTTACATGCGCGGTTCTAT

2281      AGATAACATATATCTAGCTAGATGCAGTAATATACACAGATTCCCGCGGACGTGGGAAGG
                TCTATTGTATATAGATCGATCTACGTCATTATATGTGTCTAAGGGCGCCTGCACCCTTCC

2324 SAC2,
```

```
2341  AAAAAATTAGATAACAAAATCTGAGTGATATGGAAATTCCGCTGTATAGCTCATATCTTT
      TTTTTTAATCTATTGTTTTAGACTCACTATACCTTTAAGGCGACATATCGAGTATAGAAA

2401  CCCTTCAACACCAGAAATGTAAAAATCTTGTTACGAAGGATCTTTTTGCTAATGTTTCTC
      GGGAAGTTGTGGTCTTTACATTTTTAGAACAATGCTTCCTAGAAAAACGATTACAAAGAG

2461  GCTCAATCCTCATTTCTTCCCTACGAAGAGTCAAATCTACTTGTTTTCTGCCGGTATCAA
      CGAGTTAGGAGTAAAGAAGGGATGCTTCTCAGTTTAGATGAACAAAAGACGGCCATAGTT

2521  GATCCATATCTTCTAGTTTCACCATCAAAGTCCAATTTCTAGTATACAGTTTATGTCCCA
      CTAGGTATAGAAGATCAAAGTGGTAGTTTCAGGTTAAAGATCATATGTCAAATACAGGGT

2562 SNAI,

2581  ACGTAACAGACAATCAAAATTGGAAAGGATAAGTATCCTTCAAAGAATGATTCTGCGCTG
      TGCATTGTCTGTTAGTTTTAACCTTTCCTATTCATAGGAAGTTTCTTACTAAGACGCGAC

2641  GCTCCTGAACCGCCTAATGGGAACAGAGAAGTCCAAAACGATGCTATAAGAACCAGAAAT
      CGAGGACTTGGCGGATTACCCTTGTCTCTTCAGGTTTTGCTACGATATTCTTGGTCTTTA

2701  AAAACGATAAAACCATACCAGGATCC
      TTTTGCTATTTTGGTATGGTCCTAGG

2721 BAMHI,
```

Primer #1: Spacer Deletion

```
5'                                3'
  GATTTGAAGAAAAGAGCTGAGATCACCAGG
```

Primer #2: Spacer Deletion + BssHII Site

```
5'                                3'
  GATTTGAAGAAGCGCGCTGAGATCACCAGG
              BssHII
```

FIGURE 13   Primers for Mutagenesis of the *K. lactis* α-Factor Leader

Polyacrylamide gel overlayered with a plasminogen/fibrin-agarose gel. Lane 1 contains 20 ng t-PA produced by melanoma cells (Kabi-Vitrum). In lane 2 a sample prepared from the supernatant of a CBS 2360 culture was applied and in lane 3 a sample prepared from the supernatant of a culture from CBS 2360 transformed with pGBtPA1.

Analysis of the supernatant of cultures of CBS 2360 and CBS 2360 transformed with pGBHSA3 on a 10% polyacrylamide gel according to Leammli. Lane 1 contains marker proteins (the molecular weights are indicated), lane 2 and 3 samples from the supernatants of the control strain CBS 2360 and lane 4 a sample from the supernatant of one of the transformants.

KLUYVEROMYCES AS A HOST STRAIN

This application is a Continuation of U.S. application Ser. No. 07/480,102, filed Feb. 14, 1990, now abandoned, which is a Continuation of Ser. No. 07/300,608, filed Jan. 23, 1989, now abandoned, which is a Continuation of U.S. Pat. No. 4,943,529 filed as Ser. No. 07/078,539 on Jul. 28, 1987, which is a Continuation of U.S. Pat. No. 4,859,596 filed as Ser. No. 06/572,414 on Jan. 19, 1984, which entered the National Phase of Serial No. PCT/EP83/000,128, filed May 19, 1983.

TECHNICAL FIELD

This invention relates to methods for preparing and using Kluyveromyces for the production of polypeptides of interest which preferentially are secreted into the growth medium. The invention is exemplified by sequences useful in the production of chymosin and precursors thereof, tissue plasminogen activator (t-PA), and human serum albumin (HSA), in Kluyveromyces.

BACKGROUND OF THE INVENTION

The bright promise of production of peptides in microorganisms has been tarnished by a number of factors. In many instances, where the peptide has been produced and retained in the cytoplasm, inclusion bodies have resulted requiring denaturation and renaturation of the protein, frequently with only partial or little success. In other instances, the peptide has been subjected to substantial degradation, so that not only are yields low, but also complicated mixtures are obtained which are difficult to separate. As a potential solution to these difficulties, the possibility of secretion of the desired peptide into the nutrient medium has been investigated. Secretion has met with limited success, since not all proteins have been found to be capable of secretion in the host which have been employed. Even when secreted, the processing of the peptide may result in a product which differs from the composition and/or conformation of the desired peptide. There is, therefore, substantial interest in being able to develop systems for the efficient and economic production of active peptides under conditions which allow for the use of the peptides in a wide variety of environments, both in vitro and in vivo.

RELEVANT LITERATURE

European Patent Application (EPA) 0096430 discloses Kluyveromyces as a host for cloning and expression of foreign genes. However, no mention was made of the capability of secreting proteins into the growth medium.

The leader sequence of amyloglucosidase for Aspergillus is described by Boyle et al., EMBO J. (1984) 3:1581–1585 and Innis et al., Science (1985) 228:21–26. Lactase promoters are described by Bruenig et al., Nucleic Acids Res. (1984) 12:2327–2341. The use of signal peptides associated with mating-type α-factor and of the enzymes invertase and acid phosphatase to direct the secretion of heterologous proteins in Saccharomyces has been described in EP-A-0123544 and by Smith et al., Science (1985) 229:1219.

Production of preprochymosin, prochymosin and chymosin in Saccharomyces has been studied by Mellor et al., Gene (1983) 24:1–14. When prochymosin is made intracellularly in Saccharomyces, only a low percentage of prochymosin obtained is activatable. See Moir et al. in Developments in Industrial Biology (1985) 26:75–85; Mellor et al., Gene (1983) 24:1–14; Kingsman et al. in Biotechnology and Genetic Engineering Reviews Vol. 3 (1985) 376–418. The aggregated prochymosin produced by Saccharomyces required complicated methods of denaturation and renaturation to solubilize the prochymosin. See WO 83/04418 and EP-A-0114506.

SUMMARY OF THE INVENTION

Peptide production systems are provided comprising Kluyveromyces host strains, expression cassettes which include efficient transcriptional initiation and termination regions for use in Kluyveromyces and a gene, optionally containing a signal sequence for secretion, under the transcriptional and translational regulation of the regulatory regions. The cassettes are introduced into the Kluyveromyces host strain under conditions whereby the resulting transformants stably maintain the expression cassettes. Naturally occurring DNA and synthetic genes may be employed for the production of peptides of interest.

BRIEF DESCRIPTION OF THE FIGURES

FIG. 3 is a description of the synthesized oligonucleotides for the signal sequence adapted from the amyloglucosidase signal sequence;

FIG. 4 is a description of a synthetic signal sequence;

FIG. 6 is the sequence of the entire BamHI insert from pDM100PC comprising the fusion peptide of the α-factor of S. cerevisiae and prochymosin and transcriptional regulatory regions;

FIG. 8 shows the strategy used to design oligonucleotide probes used to identify K. lactis α-factor DNA;

FIG. 9 is the complete sequence of a DNA fragment encoding the K. lactis α-factor;

FIG. 11 shows the sequences around the junctions in α-factor/prochymosin fusions;

FIG. 12 is the sequence of the BamHI/SalI insert of pAB309;

FIG. 13 represents the sequences of the primers for mutagenesis of K. lactis α-factor leader DNA;

DESCRIPTION OF THE SPECIFIC EMBODIMENTS

Figure 1:
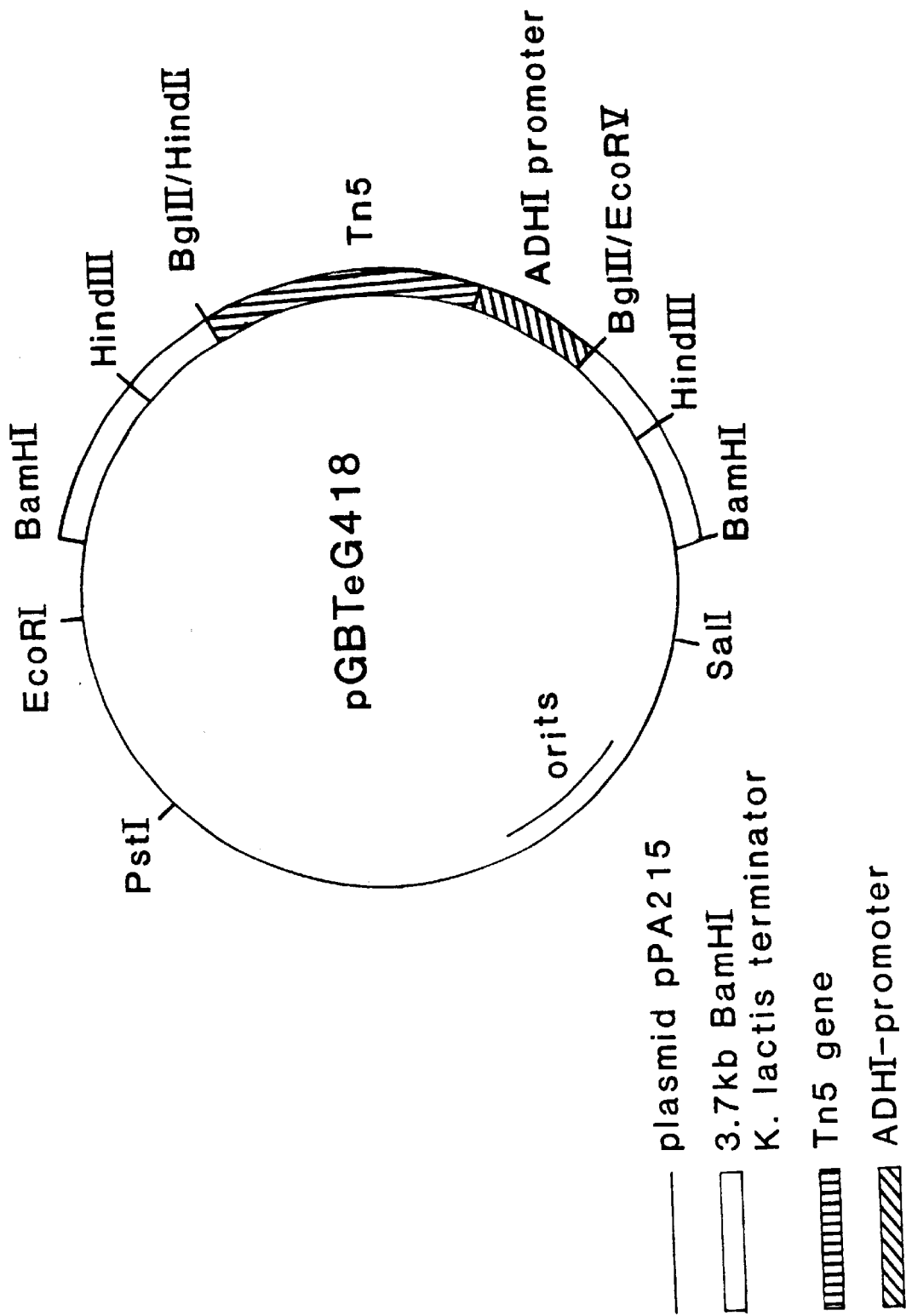
FIG. 1 is a diagram of the plasmid pGBTe418.

In accordance with the subject invention, expression cassettes are provided which allow for the efficient and economic production of polypeptides by Kluyveromyces yeast cells. The expression cassettes have transcriptional and translational regulatory sequences functional in a Kluyveromyces host cell and an open reading frame coding for a peptide of interest under the transcriptional and translational control of the regulatory regions. The open reading frame also may include a leader sequence recognized by the Kluyveromyces host which provides for secretion of the polypeptide into the growth medium. The Kluyveromyces cells used may be either laboratory or industrial strains.

The expression cassette will include in the 5'-3' direction of transcription, a transcriptional and translational initiation regulatory region, an open reading frame encoding a peptide of interest, desirably having a signal sequence for secretion recognized by Kluyveromyces, and a translational termination region. The expression cassette will further comprise a transcriptional termination regulatory region. The initiation and termination regulatory regions are functional in Kluyveromyces and provide for efficient expression of the peptide of interest without undesirable effects on the viability and proliferation of the Kluyveromyces host.

The transcriptional and translational initiation regulatory region may be homologous or heterologous to Kluyveromyces. Of particular interest are transcriptional initiation regions from genes which are present in Kluyveromyces or other yeast species, such as Saccharomyces, for example, *cerevisiae,* Schizosaccharomyces, Candida, etc., or other fungi, for example, filamentous fungi such as Aspergillus, Neurospora, Penicillium, etc. The transcriptional initiation regulatory regions may be obtained for example from genes in the glycolytic pathway, such as alcohol dehydrogenase, glyceraldehyde-3-phosphate dehydrogenase, phosphoglucoisomerase, phosphoglycerate kinase, etc., or regulatable genes such as acid phosphatase, lactase, glucoamylase, etc.

Any one of a number of regulatory sequences may be preferred in a particular situation, depending upon whether constitutive or induced transcription is desired, the particular efficiency of the promoter in conjunction with the open reading frame of interest, the ability to join a strong promoter with a control region from a different promoter which allows for inducible transcription, ease of construction, and the like. These regulatory regions find ample precedent in the literature. See, for example, EP-A-0164566, incorporated herein by reference.

Secretion of heterologous proteins in genetically modified microorganisms is generally accomplished by one of two methods. In the first, the leader sequence is homologous to the protein; in the second, the leader sequence is homologous to the host organism. Other alternatives of particular interest in the present invention for secretion of heterologous proteins in Kluyveromyces include the use of a leader sequence heterologous to both Kluyveromyces and the peptide of interest, or a synthetic leader sequence specifically designed. The DNA encoding the former leader sequence can be obtained by isolation or made synthetically. Thus, the open reading frame usually will include a wild-type or mutated gene, where the signal sequence is normally associated with the remainder of the coding sequence, a hybrid or chimeric open reading frame, where the signal sequence is normally not associated with the remaining portion of the open reading frame, or a synthetic sequence, where the signal sequence and the remainder of the open reading frame are synthesized to provide for preferred codons, convenient restriction sites, novel amino acid sequences, and the like, or combinations thereof. Signal sequences which may be employed may be obtained from genes, such as α-factor, invertase, amyloglucosidase, native or wild type signal sequences present in structural genes and recognized by Kluyveromyces, Saccharomyces, other fungi, e.g. Neurospora, Aspergillus, and other eukaryotes.

Of particular interest is the use of a signal sequence which provides for secretion of the peptide of interest into the nutrient medium, rather than into the periplasmic space. For the most part, the signal sequence will be the 5'-terminus of the open reading frame. However, in some situations, it may be desirable to have the signal sequence internal to the open reading frame. For use of internal signal sequences for secretion, see U.S. Pat. No. 4,338,397 and Perara and Lingappa, J. Cell Biology (1985) 101:2292–2301. Genes into which the open reading frame of interest may be inserted include highly expressed constitutive genes, for example, genes encoding enzymes of the glycolytic pathway, or highly expressed regulatable genes such as lactase, amyloglucosidase, or the like.

For optimal gene expression, the nucleotide sequences surrounding the translational initiation codon ATG have been found to be important in yeast cells and in animal cells. For example, M. Kozak, Microbiol. Revs. (1983) 47:1–45 has studied extensively the effect of these regions on the expression of insulin in COS cells. Similarly, some specific nucleotides are found more frequently than others in the genes for highly expressed yeast proteins, indicating the important effect of these nucleotides on the level of expression of these genes.

For optimal gene expression of exogenous genes it will be important to modify the nucleotide sequences surrounding the initiation codon ATG. This can be done by site-directed mutagenesis or by fusing the exogenous gene in frame to an endogenous Kluyveromyces gene, preferably a highly expressed gene, such as the lactase gene.

Normally, it will be desirable to provide that the signal leader is cleaved from the peptide of interest during the secretory process, rather than subsequent to the secretory process, although either procedure may find use. Usually, the processing signal employed will be the processing signal naturally occurring with the signal sequence or a processing signal which has been modified from the naturally occurring one, which is still effective for providing for a peptide signal resulting in hydrolytic cleavage of the signal peptide and processing signal peptide from the peptide of interest. Various processing signals have been sequenced and defined, such as α-factor (see for example U.S. Pat. No. 4,546,082, which is incorporated herein by reference), amyloglucosidase, α-amylase, etc. In some instances, other peptidase-recognized sequences may be employed which may require subsequent cleavage for isolation of the desired peptide. These sequences include dibasic peptides, e.g. KR, $(D)_4K$, and EA, which are cleaved by KEX2, bovine enterokinase, and a yeast membrane peptidase, respectively.

The peptide of interest may be native to the host or heterologous, being derived from prokaryotic or eukaryotic sources, which eukaryotic sources may involve fungi, protists, vertebrates, non-vertebrates, and the like. The peptide products may include enzymes, such as lactase, α-amylase, β-amylase, amyloglucosidase, chymosin, etc., mammalian peptides, such as hormones, interleukins, cytokines, cachexin, growth factors, e.g. platelet derived, epidermal, skeletal, etc., growth hormone, follicle stimulating hormone, interferons (α-, β-, and γ-), blood factors such as factor V, VI, VII, VIII (vW or c), IX, X, XI or XII, plasminogen activator (tissue or urinary), serum albumin, e.g. human serum albumin, colony growth factor (e.g. GM), erythropoietin, thaumatin, insulin, etc.

These structural genes may be obtained in a variety of ways. Where the amino acid sequence is known, the structural gene may be synthesized in whole or in part, particularly where it is desirable to provide yeast-preferred codons. Thus, all or a portion of the open reading frame may be synthesized using codons preferred by Kluyveromyces. Preferred codons may be determined by those codons which are found in the genes for proteins produced in greatest amount by the Kluyveromyces host e.g. glycolytic enzymes. Methods for synthesizing sequences and bringing the sequences together are well established in the literature. Where a portion of the open reading frame is synthesized, and a portion is derived from natural sources, the synthesized portion may serve as a bridge between two naturally occurring portions, or may provide a 3'-terminus or a 5'-terminus. Particularly where the signal sequence and the open reading frame encoding the peptide are derived from different genes, synthetic adaptors commonly will be employed. In other instances, linkers may be employed, where the various fragments may be inserted at different restriction sites or substituted for a sequence in the linker.

For the most part, some or all of the open reading frame will be from a natural source. Methods for identifying sequences of interest have found extensive exemplification in the literature, although in individual situations, different degrees of difficulty may be encountered. Various techniques involve the use of probes, where at least a portion of the naturally occurring amino acid sequence is known, where genomic or cDNA libraries may be searched for complementary sequences. Alternatively, differential transcription can be detected when the gene of interest can be induced or when cells are from the same host but of different differentiation, by comparing the messenger RNA's produced. Other techniques have also been exemplified.

The termination region may be derived from the 3'-region of the gene from which the initiation region was obtained or from a different gene. A large number of termination regions are known and have been found to be satisfactory in a variety of hosts from the same and different genera and species. The termination region is usually selected more as a matter of convenience rather than because of any particular property. Preferably, the termination region will be derived from a yeast gene, particularly Saccharomyces or Kluyveromyces.

In developing the expression cassette, the various fragments comprising the regulatory regions and open reading frame may be subjected to different processing conditions, such as ligation, restriction, in vitro mutagenesis, primer repair, use of linkers and adaptors, and the like. Thus, nucleotide transitions, transversions, insertions, deletions, or the like, may be performed on the DNA which is employed in the regulatory regions and/or open reading frame.

During the construction of the expression cassette, the various fragments of the DNA will usually be cloned in an appropriate cloning vector, which allows for addition to the inserted DNA, modification of the DNA or manipulation by joining or removing of the sequences, linkers, or the like. Normally, the vectors will be capable of replication in at least a relatively high copy number in *E. coli*. A number of vectors are readily available for cloning, including such vectors as pBR322, pACYC184, pUC7-19, M13, Charon 4A, and the like.

The cloning vectors are characterized by having an efficient replication system functional in *E. coli*. Also, the cloning vector will have at least one unique restriction site, usually a plurality of unique restriction sites and may also include multiple restriction sites, particularly two of the same restriction sites for substitution. In addition, the cloning vector will have one or more markers which provide for selection for transformants. The markers will normally provide for resistance to cytotoxic agents such as antibiotics, heavy metals, toxins or the like, complementation of an auxotrophic host, or immunity to a phage. By appropriate restriction of the vector and cassette, and, as appropriate, modification of the ends, by chewing back or filling in overhangs, to provide for blunt ends, by addition of linkers, by tailing, complementary ends can be provided for ligation and joining of the vector to the expression cassette or component thereof.

After each manipulation of the DNA in the development of the cassette, the plasmid will be cloned and isolated and, as required, the particular cassette component analyzed as to its sequence to ensure that the proper sequence has been obtained. Depending upon the nature of the manipulation, the desired sequence may be excised from the plasmid and introduced into a different vector or the plasmid may be restricted and the expression cassette component manipulated, as appropriate.

In some instances a shuttle vector will be employed where the vector is capable of replication in different hosts requiring different replication systems. This may or may not require additional markers which are functional in the two hosts. Where such markers are required, these can be included in the vector, where the plasmid containing the cassette, the two replication systems, and the marker(s) may be transferred from one host to another, as required. In the present situation, the second replication system would be a replication system functional in Kluyveromyces. The replication systems which may be used may be derived from plasmids, e.g. pKD1 from *Kluyveromyces drosophilarum*, viruses, or the chromosome of Kluyveromyces or other species, particularly one associated with Kluyveromyces, such as Saccharomyces. Thus, replication systems include the replication system of the 2 micron plasmid found in Saccharomyces and an autonomously replicating sequence (ARS) gene, for example when used in conjunction with a centromere sequence, or the like. If desired, regions of homology may be provided to encourage integration of the expression cassette into the genome of the Kluyveromyces host.

Of particular interest in the constructs of the subject invention is a sequence derived from Kluyveromyces DNA chromosomes referred to as KARS, which provide for high transformation frequency. The KARS gene may be obtained by screening a library of Kluyveromyces DNA fragments for enhanced transformation efficiency. In this manner, fragments can be obtained which contain KARS sequences, which fragments can be further modified by restriction, or primer repair, to provide a fragment of approximately 200 bp and not more than about 5000 bp, more usually from about 200 bp to 2000 bp which provides for enhanced transformation efficiency. The presence of the KARS gene can provide transformation of *K. lactis* auxotrophic species to prototophy at a frequency of at least about $10^3$ per microgram of DNA, usually at a frequency of $10^4$ per microgram of DNA or higher.

The manner of transformation of *E. coli* with the various DNA constructs (plasmids and viruses) for cloning is not critical to this invention. Conjugation, transduction, transfection or transformation, e.g. calcium chloride or phosphate mediated transformation, may be employed. By contrast, for yeast, for the most part the prior art has relied on transformation of protoplasts employing combinations of calcium ions and polyethylene glycol of from about 2000 to 8000, usually 4000 to 7000 daltons.

An alternative method of transformation involves growing Kluyveromyces in a standard yeast nutrient medium to a density of 1 to 25, desirably 4 to 10 $OD_{610}$. The Kluyveromyces cells are then harvested, washed and pretreated with chaotropic ions, particularly the alkali metal ions lithium, cesium or rubidium, particularly as the chloride or sulfate, more particularly the lithium salts, at concentrations of about 2 mM to 1M, preferably about 0.1 M. After incubating the cells with the chaotropic ion(s), the DNA is added and the incubation is prolonged for a short period of time at a moderate temperature, generally from about 20° C. to 35° C., for about 5 to 60 min. Then polyethylene glycol is added, desirably at a concentration to about 25 to 50%, where the entire medium may be diluted by adding an equal volume of a polyethylene glycol concentrate to result in the desired final concentration. The polyethylene glycol will be of from about 2000 to 8000 daltons, preferably about 4000 to 7000 daltons. Incubation will generally be for a relatively short time, generally from about 5 to 60 min. Desirably, the incubation medium is subjected to a heat treatment of from about 1 to 10 min. at about 35° C. to 45° C., preferably about 42° C.

For selection, any useful marker may be used, although the number of markers useful with Kluyveromyces is narrower than the markers used for Saccharomyces. Desirably, resistance to kanamycin and the aminoglycoside G418 are of interest, as well as complementation of a gene in the tryptophan metabolic pathway, particularly TRP1 or in the lactose metabolic pathway, particularly LAC4.

Although a marker for selection is highly desirable for convenience, other procedures for screening transformed cells have been described. See for example G. Reipen et al., Current Genetics (1982) 5:189–193. Besides the use of an indicator enzyme such as β-lactamase, transformed cells may be screened by the specific products they make. In the case of chymosin, for example, synthesis of the product may be determined by an immunological or an enzymatic method.

The vector used may be capable of extrachromosomal maintenance in Kluyveromyces or result in integration into the Kluyveromyces genome. It has been found that the 2 micron plasmid replication system from Saccharomyces provides for extrachromosomal maintenance in Kluyveromyces. In addition, one may use a combination of a centromere, such as the Saccharomyces CEN3 and a high transformation frequency sequence, such as ARS or KARS. If selective maintenance is provided, such as complementation or resistance to an antibiotic to which Kluyveromyces is susceptible, the ARS-like sequences will usually suffice for extrachromosomal maintenance.

For large scale fermentation even a small loss of plasmid stability will greatly affect the final yield of the desired protein. To increase the stability of recombinant molecules in host cells, for example Kluyveromyces, integration of the recombinant molecules into the host chromosome may be used.

Where integration is desired, it will usually be desirable to have a sequence homologous to a sequence of the chromosome of the host, so that homologous recombination may occur. It is understood, that random integration also occurs, so that the homologous sequence is optional. Where an homologous sequence is employed, the homologous sequence will usually be at least about 200 bp and may be 1000 bp or more. In addition, where integration is involved, one may wish to have amplification of the structural gene. Amplification has been achieved by providing for a gene in tandem with the desired structural gene, which provides for selective advantage for the host in a selective medium. Thus, the genes expressing dihydrofolate reductase, metallothioneins, thymidine kinase, etc., have proven useful in a variety of hosts to provide for amplification, where the gene provides protection from a toxin, such as methotrexate, heavy metals, such as copper and mercury, and the like.

Vectors of interest providing for stable replication include KARS vectors originating from *K. lactis*, e.g. pKARS12 and pKARS2, which plasmids comprise a *K. lactis* DNA fragment containing the KARS12 or KARS2 sequence in the *S. cerevisiae* plasmid YRp7. A vector employed for integration is, for example, pL4, a hybrid plasmid of the ARS1 carrying plasmid YRp7 and *K. lactis* XhoI DNA fragment carrying the LAC4 gene. See EP-A 0096430.

Plasmids of particular interest include plasmids having the 2 micron plasmid replication system, the LAC4 gene, the Tn601 and Tn5 kanamycin resistance gene, which also provides resistance to the antibiotic G418 in Kluyveromyces (Jimenez and Davis, Nature (1980) 287:869–871). This plasmid provides for autonomous replication in Kluyveromyces and can be selected for by resistance to G418 on regeneration plates containing glucose, sorbitol, and 0.2 μg/ml G418, while avoiding elevated concentrations of KCl, which interferes with the sensitivity of Kluyveromyces to G418. Preferred plasmids include the TRP1 gene, particularly from *S. cerevisiae*, the LAC4 gene, particularly from *K. lactis*, the Kan$^R$ gene providing for resistance against antibiotic G418 from Tn5, or the like.

The subject vectors and constructs are introduced into an appropriate host for cloning and expression of the desired structural genes. After transformation, colonies will normally appear on regeneration medium within about 5 to 6 days. Where an antibiotic is employed for selection, the colonies should be screened to ensure the absence of spontaneous mutation to a resistant strain. Employing the plasmids and the methods of the subject invention, about 5% of resistant colonies were found to contain the plasmid construct providing for at least about 4 transformants per μg of plasmid DNA. Where selection was based on the presence of the LAC4 gene, using plates containing lactose as the sole carbon source and 0.6M KCl as an osmotic stabilizer, all of the surviving colonies were found to be transformants and not spontaneous revertants. About 20 transformants were obtained after about 4 to 5 days of incubation at moderate temperature, e.g. 30° C.

As a host organism, Kluyveromyces is especially suitable for the production of heterologous proteins, for example for the production and extraction of the enzyme chymosin and its precursors preprochymosin, pseudochymosin and prochymosin, for human serum albumin (HSA), tissue plasminogen activator (t-PA), and thaumatin and its precursor forms. Although other organisms such as Saccharomyces produce prochymosin in reasonable amounts, the produced prochymosin cannot be extracted in an active or activatable form. We have surprisingly found that more than 90% of the total amount of the prochymosin produced by Kluyveromyces can be extracted in an active form with very simple standard techniques.

Any of the many Kluyveromyces species may be employed. Either laboratory or industrial, preferably industrial, strains may be used. By industrial species is intended, Kluyveromyces strains from organisms which may be isolated from natural sources or may be available from depositories or other sources or obtained by modification, e.g. mutation, of such strains. The industrial strains are characterized by being resistant to genetic exchange, being prototrophic or made prototrophic by a single gene being introduced into the host strain, and are usually selected for improved production of peptides. Among the Kluyveromyces species which may find use are *K. lactis, K. fragilis, S. bulgaricus, K. thermotolerans, K. marxianus,* etc. It should be further noted that the Kluyveromyces organisms are on the GRAS (Generally Recognized As Safe) list. Their use for production of products to be used in vivo or to be ingested normally will not require special governmental review and approval.

Both wild type and mutant Kluyveromyces, particularly *Kluyveromyces lactis* or *Kluyveromyces fragilis* may be employed as hosts. Hosts of particular interest include *K. lactis* SD11 lac4 trp1 and *K. lactis* SD69 lac4, and the wild-type strain CBS 2360 (see EP-A-0096430).

For maintaining selective pressure on the transformants for maintenance of the plasmids, selective media may be used, such as a yeast nitrogen-based medium, 2% lactose instead of glucose for *K. lactis* SD69 lac4 (PTY75-LAC4) and for *K. lactis* SD69 lac4 (pL4) and a yeast nitrogen-based medium (Difco) plus 2% glucose for *K. lactis* SD11 lac4 trp1 (pKARS12). See for the transformants mentioned, EP-A-0096430. Similarly, strains containing plasmids conferring antibiotic resistance, for example against G418, may be cultivated in a medium containing said antibiotic.

Where the hybrid plasmids are employed for large. scale production of the desired protein, it would generally be useful to remove at least substantially all of the bacterial DNA sequences from the hybrid plasmids.

Depending upon the nature of the structural gene of interest, the expression product may remain in the cytoplasm of the host cell or be secreted. It has been found that not only the proteins that remain in the cell but also those that are secreted are soluble. Where the expression product is to remain in the host cell, it may generally be desirable to have an inducible transcription initiation region, so that until the transformant has reached a high density, there is little or no expression of the desired product. After sufficient time for the expression product to form, the cells may be isolated by conventional means, e.g. centrifugation, lysed and the product of interest isolated. Depending upon the nature and use of the product, the lysate may be subjected to various purification methods, such as chromatography, electrophoresis, solvent extraction, crystallization, or the like. The degree of purity may vary from about 50%, to 90% or higher, up to essential purity.

When the product is to be secreted, both constitutive and non-constitutive transcriptional initiation regions may be employed, depending on the fermentation process used for the production of the protein or polypeptide of interest. The expression product may be secreted into the culture medium, and produced on a continuous basis, where the medium is partially withdrawn, the desired product extracted, e.g., by affinity chromatography, or the like, and the spent medium discarded or recirculated by restoring essential components.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following examples are offered by way of illustration and not by limitation.

EXPERIMENTAL

Example 1

Construction of Chymosin Expression Plasmids Containing a Long Lactase Promoter Sequence A. Construction of pUCla56

Chromosomal DNA was isolated from *Kluyveromyces lactis* strain CBS 2360 (Das and Hollenberg, Current Genetics (1982) 5:123–128), cleaved with XhoI, and separated according to size on a sucrose gradient. Fractions containing the lactase gene were detected with a LAC4 probe from plasmid pK16 after spotting the DNA on a nitrocellulose filter (see EP-A-0096430, Example 16.C2). DNA containing the LAC4 gene was cloned into the SalI site of plasmid pPA153-215 (Andreoli, Mol. Gen. Genet. (1985) 199:372–380) giving rise to plasmid pPA31. An XbaI fragment of pPA31 containing the lactase gene was subcloned in the XbaI site of pUC19 (Yanisch-Perron et al., Gene (1985) 33: 103–119) which yields plasmid pUCla56.

B. Introduction of the G418 Resistance Gene in the Terminator of the Lactase Gene The terminator fragment containing the G418 resistance marker was obtained from plasmid pGBTeG418. *E. coli* containing pGBTeG418 was deposited with Centraal Bureau voor Schimmelcultures under number CBS 184.87 on Feb. 26, 1987. Plasmid pGBTeG418 (see FIG. 1) consists of the plasmid pPA153-215, as described above, and a 5.6 kb fragment consisting of the 3.7 kb BamHI *K. lactis* lactase terminator fragment (Breuning et al., Nucl. Acid Res. (1984) 12:2327–2341) and the Tn5 gene (Reiss et al., EMBO J. (1984) 3:3317) conferring resistance to G418 under the direction of the promoter alcohol dehydrogenase I (ADH) from yeast, similar to that described by Bennetzen and Hall, J. Biol. Chem. (1982) 257:3018–3025.

C. Construction of Plasmid pGB900 Containing the G418 Resistance Gene and Prochymosin Encoding DNA The 3.6 kb HindIII-XbaI fragment from plasmid pGBTeG418 containing the G418 resistance gene (see Example 1B) and the SalI-HindIII fragment containing the prochymosin gene from pGB123 (see EP-A-0096430) were ligated in pUC19 cleaved with SalI and XbaI. This yielded plasmid pGB900.

Figure 2:
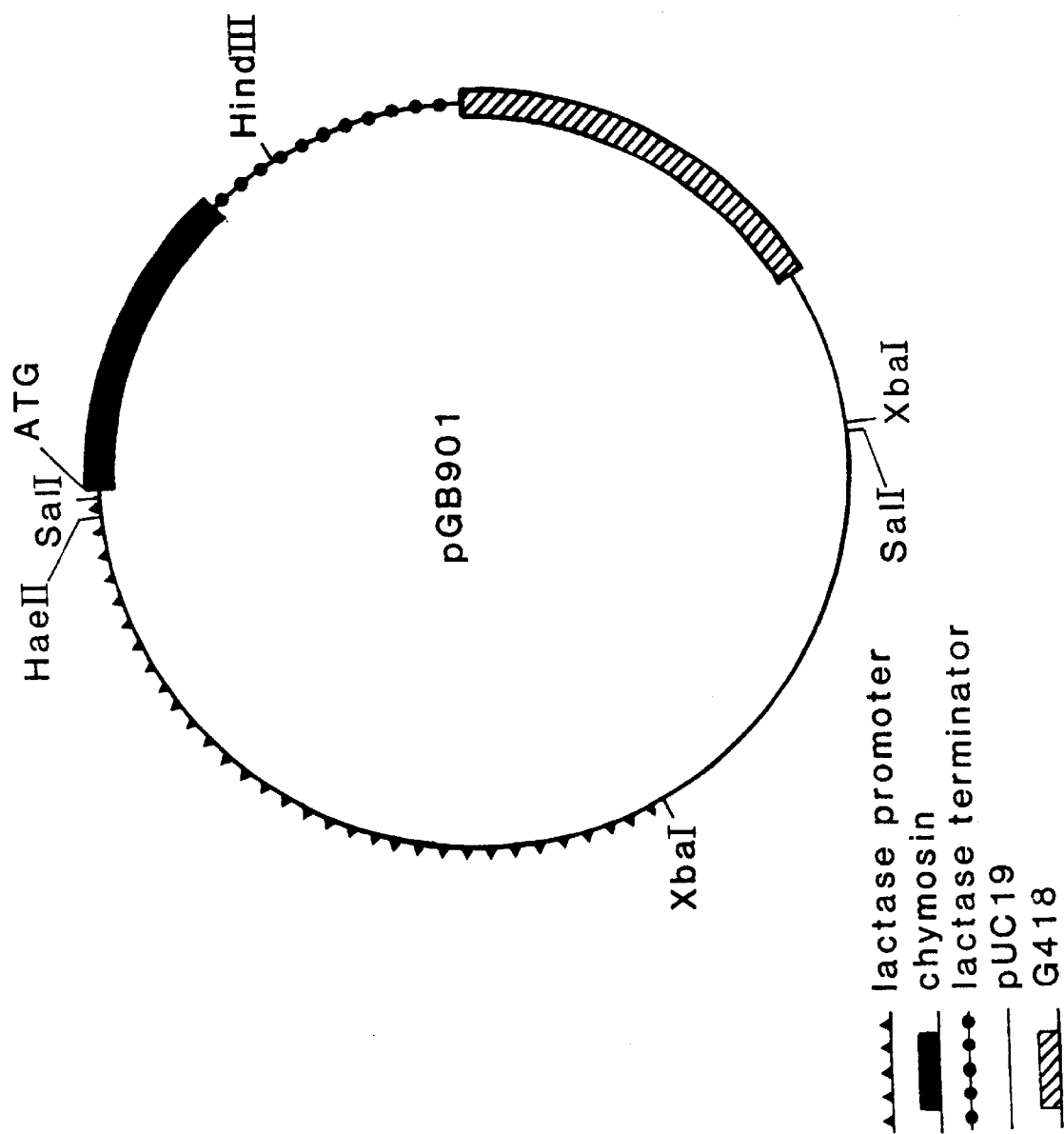
FIG. 2 is a diagram of the plasmid pGB901.

D. Construction of Plasmid pGB901 (See FIG. 2)

Plasmid pGB901 was constructed by ligating the following four fragments:
(1) a 3.6 kb XbaI-HaeII fragment containing the lactase promoter to about position −90 from the lactase ATG start codon isolated from pUCla56,
(2) a HaeII-SalI fragment extending from the above HaeII site to a SalI site, which was ligated to position −26 in a similar Bal31 experiment as described in Example 16.C2 of EP-A-0096430. However, in this experiment only a SalI linker was used. This fragment has the following sequence.
5' TTAAC ACTTGAAATT TAGGAAAGAG CAGAATTTGG CAAAAAAAAT AAAAAAAAAA TAAACACG 3'
3' CGCGAATTG TGAACTTTAA ATCCTTTCTC GTCTTAAACC GTTTTTTTTA TTTTTTTTT ATTTGTGCAG CT 5'

(3) the 5.1 kb SalI-XbaI fragment containing prochymosin and G418 from pGB900 (see Example 1C), (4) pUC19 cleaved with XbaI.

During the construction of the plasmid the CG sequence from the HaeII site was inadvertently removed, thereby creating a HindIII site at this position.

Prochymosin-encoding DNA is present in plasmid pGB901. This may readily be converted to plasmids with preprochymosin, pseudochymosin or chymosin DNA by using the SalI-BglII fragments from pGB 131, 122 or 124, respectively (see EP-A-0096430).

Example 2

Secretion of Prochymosin from *Kluyveromyces lactis* Transformants

To direct the synthesis of prochymosin in Kluyveromyces, plasmid pGB901 was used to transform *K. lactis* strains SD11 and CBS 2360 with similar results. The transformation was carried out essentially as described in Examples 4 and 14 of EP-A-0096430, by using intact plasmid DNA or plasmid DNA cut with restriction endonucleases. In the latter case restriction endonucleases were used which cut in the promoter region, e.g., SacII, NdeI, SnaBI or SpeI, or in the terminator region, e.g., EcoRV, or both the promoter and terminator regions.

*K. lactis* strain CBS 2360 was grown in 100 ml of YEPD-medium (1% yeast extract, 2% peptone, 2% glucose) containing 2.5 ml of a 6.7% yeast nitrogen base (Difco) solution to an $OD_{610}$ of about 7. The cells were collected by centrifugation from 10 ml of the culture, washed with TE-buffer (10 mM Tris-HCl pH 7.5, 0.1 mM EDTA) and resuspended in 1 ml TE-buffer. An equal volume of 0.2 M lithium acetate was added and the mixture was incubated for 1 hr at 30° C. in a shaking waterbath. Plasmid pGB901 (15 µg) was cut at the unique SacII site in the lactase promoter, ethanol precipitated and resuspended in 15 µl TE-buffer. This DNA preparation was added to 100 µl of the pre-incubated cells and the incubation was prolonged for 30 minutes. Then an equal volume of 70% PEG 4000 was added and the mixture was incubated for 1 hr at the same temperature, followed by a heatshock of 5 minutes at 42° C. Then 1 ml of YEPD-medium was added and the cells were incubated for 1.5 hrs in a shaking waterbath of 30° C. Finally the cells were collected by centrifugation, resuspended in 300 µl YEPD and spread on agar plates containing 15 ml of YEPD agar with 300 µg/ml of G418, overlayered (1 hr before use) with 15 ml YEPD-agar without G418. Colonies were grown for 3 days at 30° C. *K. lactis* strain SD11 was transformed in a similar way, only the initial G418 concentration in the selection plates was lowered to 150 µg/ml. In one of the experiments transformants of CBS 2360 were grown at 30° C. in YEP-medium containing 2% galactose. After 60 hours, cells and medium were separated by centrifugation. Cells were disrupted by treatment with glass beads. Culture medium and cell extract were treated at pH 2 before assaying for chymosin activity (see Foltman, Methods in Enzymology (1970) 19:421–426).

Cells were removed from cultures by centrifugation and the resulting supernatants were acidified to pH 2 by the addition of 1 M $H_2SO_4$ and incubated for 2 hours at room temperature. The solutions were then neutralized to pH 6 by the addition of 2 M Tris base. A 50 µl volume of an appropriate dilution was added to a suspension of 12% non-fat dry milk in 10 mM $CaCl_2$ and incubated at 37° C. until a clot formed. A unit of chymosin activity is defined as the amount of active chymosin required to produce a clot in 10 min. under these conditions. The supernatant contained milk-clotting activity due to the production and secretion of prochymosin by *K. lactis* transformants although no signal sequence for protein secretion was added to prochymosin. About 30–60% of the total prochymosin produced was found in the medium as determined by the above-described milk-clotting assay. Similar results were obtained when *K. lactis* strain SD11 was used.

Example 3

Lactase-chymosin Fusion Proteins Giving Enhanced Chymosin Production

By taking various SnaBI-SalI fragments (from a Bal31 experiment similar to the one described in Example 16.C2 of EP-A-0096430 but using a single SalI linker only) variants of pGB901 containing a fusion between the lactase and chymosin proteins were obtained (Table 1). The extra amino acids provided by lactase DNA and linker sequences can be removed, along with the pro sequence of prochymosin, by treatment with acid. It was observed that a fusion containing 4 amino acids from the lactase coding sequence (pGB902) resulted in enhanced chymosin production.

TABLE 1

Nucleotide sequence at the junction between the lactase promoter and prochymosin in pGB901 and pGB902

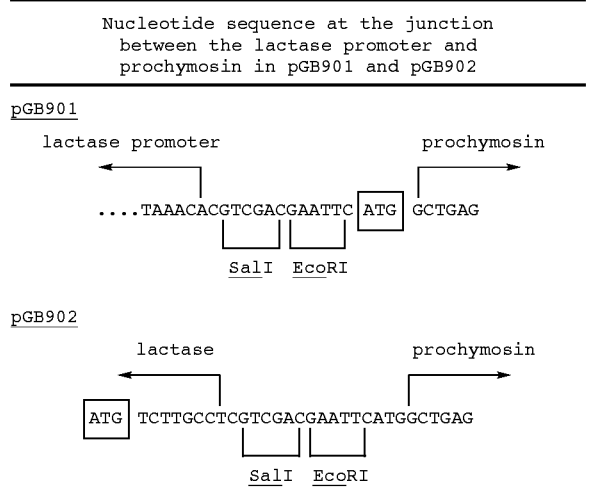

Protein synthesis starts at the boxed ATG codon.

Example 4

Expression of Preprochymosin by Kluyveromyces Transformants

The SalI site from the polylinker of pGB902 (see Example 3) was removed for convenience. pGB902 was partially digested with SalI, followed by a short incubation with Bal31 (Boehringer). Linear fragments were isolated from an agarose gel, ligated and transformed into *E. coli*. A correct plasmid, pGB903, was obtained. Restriction analysis showed that this plasmid also has the XbaI and HindIII sites removed from the polylinker.

To construct a plasmid containing and expressing preprochymosin, plasmid pGB903 was digested with the restriction endonucleases SalI and BglII. The 11 kb DNA fragment was isolated from an agarose gel by electroelution. Similarly, plasmid pGB124 containing the preprochymosin gene (see EP-A-0096430, Example 16) was digested and the 0.3 kb SalI-BglII fragment containing the N-terminal part of the preprochymosin gene was isolated.

The 11 kb and the 0.3 kb DNA fragments were mixed, ligated with DNA ligase and transformed into E. coli. Plasmid pGB904 was isolated which contained the preprochymosin gene fused to a small part of the lactase gene (Table 2).

TABLE 2

Nucleotide sequence at the junction between the lactase promoter and preprochymosin in pGB904

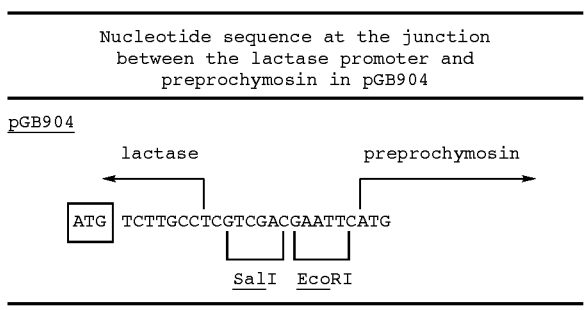

Protein synthesis starts at the boxed ATG codon.

K. lactis CBS 2360 cells were transformed with pGB904, which had been linearized with SacII. Transformants were selected, grown and assayed for chymosin activity as described in Example 2. In the following Table 3 a comparison is made between the secretion of prochymosin from K. lactis CBS 2360 cells transformed with pGB902 (see Example 3) and with pGB904. (Pro)chymosin production is expressed in arbitrary units per ml of cells at $OD_{610}$ of 200.

TABLE 3

Secretion of prochymosin by K. lactis cells transformed with pGB902 and pGB904

| Transformant | pGB902 | | pGB904 | |
|---|---|---|---|---|
| | Supernatant | Pellet | Supernatant | Pellet |
| 1 | 3.2 | <0.4 | 22.4 | 1.7 |
| 2 | 1.3 | <0.4 | 33.3 | 3.0 |
| 3 | 7.1 | 1.4 | 28.0 | 2.3 |
| 4 | 4.4 | 0.66 | 53.8 | 5.8 |

Example 5

Secretion of Prochymosin by Kluyveromyces Using Heterologous Leader Sequences

A. Chemical Synthesis of an Amyloglucosidase Leader Sequence and Construction of a Plasmid Containing Said Leader Sequence The leader sequence of amyloglucosidase (AG) from Aspergillus awamori was published by Innis et al., Science (1985) 228:21–26. Based on the protein sequence, oligonucleotides were derived to permit insertion of the leader sequence in front of the prochymosin gene (see FIG. 3).

The oligonucleotides were synthesized with an Applied Biosystems DNA synthesizer. The oligonucleotides were purified by electrophoresis on a denaturing polyacrylamide gel, then electroeluted from the gel.

Plasmid pGB903 (see Example 4) was cut at the unique SalI site. The oligonucleotides were hybridized at 65° C., 50° C. and 37° C. for one hour each in 2×SSC. The oligonucleotides had no phosphate at the 5' end to prevent formation of multimers. The DNA was ligated into the SalI site using T4 polynucleotide ligase. The ligation mixture was transformed into E. coli HB101. Twenty-four of the colonies were cultured and plasmid DNA isolated. One of the plasmids, pGB905, was shown to have the correct orientation of the oligonucleotides by restriction enzyme analysis. Plasmid pGB905 was transformed to K. lactis CBS 2360. (Pro)chymosin production was analyzed according to the procedure described in Example 2. The results are of the (pro)chymosin production, in arbitrary units/ml of cells at $OD_{610}$ of 200, is shown in the following Table 4.

TABLE 4

Secretion of prochymosin by K. lactis cells transformed with pGB902 and pGB905

| Transformant | pGB902 | | pGB905 | |
|---|---|---|---|---|
| | Supernatant | Pellet | Supernatant | Pellet |
| 1. | 3.2 | <0.4 | 60.6 | <0.4 |
| 2. | 1.3 | <0.4 | 56.4 | <0.4 |
| 3. | 7.1 | 1.4 | 56.7 | <0.4 |
| 4. | 4.4 | 0.66 | 57.6 | <0.4 |

B. Chemical Synthesis of a Novel Synthetic Leader Sequence into Construction of a Plasmid Containing the Novel Synthetic Leader Sequence A synthetic leader sequence was prepared which has a sequence different from any known leader sequence. Using this leader sequence, all prochymosin synthesized was secreted by Kluyveromyces as shown below.

Figure 5:
FIG. 5 is an immunoblot showing the secretion of prochymosin by K. lactis.

This synthetic leader sequence was devised using frequently occurring amino acids from position −6 to +2 of the signal sequence cleavage site (Von Heyne, Eur. J. Biochem. (1983) 133:17–21). Frequently occurring yeast codons were also employed and extra nucleotides were incorporated in front of the ATG sequence to make up for the deletion of 26 nucleotides in pGB902. The oligonucleotides used and the resulting leader sequence are shown in FIG. 5.

The synthetic leader sequence DNA was synthesized using an Applied Biosystems DNA synthesizer. The resulting oligonucleotides were run on a 40 cm long, 1 mm thick polyacrylamide gel, containing TBE buffer (50 mM Tris, 50 mM borate, 1 mM EDTA, pH 8.3) and 7 M urea until the Bromophenol Blue marker had travelled 2/3 of the gel length. The DNA was visualized, eluted from the gel and precipitated with ethanol.

Also from pGB901 a derivative was made with a deletion around the SalI site resulting from the polylinker of pUC19. This was done by replacing the 0.5 kb SnaBI-BglII fragment from pGB903 by the corresponding fragment from pGB901. The resulting plasmid was cut at the unique SalI site. The oligonucleotides were hybridized at 65° C., 50° C. and 37° C. for one hour each in 2×SSC. The DNA was ligated into the SalI site using T4 polynucleotide ligase. The plasmid was then transformed into E. coli HB101. Of the colonies obtained, 24 were cultured and plasmid DNA isolated. One of the plasmids, pGB906, was shown to have the oligonucleotides in the correct orientation by restriction enzyme digestion. It was found that K. lactis CBS 2360 transformed with pGB906 secreted more than 95% of the prochymosin produced.

C. Analysis of Chymosin Protein Produced by K. lactis Transformed with pGB905

K. lactis CBS 2360 (pGB905) transformants were grown for 3 days at 30° C. and samples were collected from the supernatant of the cultures. Protein samples were electrophoresed on a polyacrylamide gel according to Laemmli (Nature (1970) 227:680–685). Proteins were blotted onto a nitrocellulose filter according to the method of Towbin et al. (Proc. Natl. Acad. Sci. USA (1979) 76:4350–4354). Chymosin protein was detected by incubating the filter with a polyclonal antiserum against chymosin (Chr. Hansen), followed by donkey anti-rabbit antibodies coupled to a peroxidase (Amersham) and finally with 0.6 mg/ml 4-chloronaphthol and 0.015% hydrogen peroxide in a buffer solution (50 mM Tris-HCl pH 7.5, 0.9% NaCl) containing 40% methanol. Prochymosin excreted by the AG signal sequence is correctly cleaved after pH 2 treatment as demonstrated by this assay (FIG. 5). Similar results were obtained with K. lactis CBS 2360 (pGB906) transformants.

Example 6

Construction of Plasmids Containing the Saccharomyces cerevisiae α-factor Sequence for Efficient Secretion A. Saccharomyces α-factor Expression Plasmids 1. Construction of Plasmids pDM100-PC: The starting material was plasmid pGB163 (see EP-A-0096430, Example 16.C1). Plasmid pGB163 was digested with BamHI and ligated to an XbaI-BamHI, α-factor leader-prochymosin adaptor. The resulting mixture was then treated with PstI and a 96 bp fragment encoding the pro-α-factor processing site and the N-terminal region of prochymosin was isolated. A 1900 bp fragment encoding bovine prochymosin was isolated from plasmid pJS111 following digestion with PstI and SalI. Plasmid pJS111 is a pBR322 derivative containing the prochymosin gene from pGB163 under the regulatory control of the ADH-2 promoter and the glyceraldehyde 3-phosphate (GAPDH) terminator. The 1900 bp PstI to SalI fragment that was removed contains the prochymosin gene and the GAPDH terminator. The yeast GAPDH 49 gene promoter and transcription terminator are essentially as described by Travis, J. Biol. Chem. (1985) 260:4384–4389.

Plasmid pDM100, containing a fusion of the GAPDH promoter, the S. cerevisiae α-factor leader, and a synthetic gene for human-interferon flanked by XbaI and SalI sites and the α-factor terminator, was digested with XbaI and SalI, treated with alkaline phosphatase, then ligated to the 96 bp and 1900 bp fragments described above. The α-factor leader and terminator are essentially as described by Brake, Proc. Natl. Acad. Sci. USA (1984) 81:4642–4646. The resulting plasmid pDM100-PC was isolated and contained a fusion of the GAPDH promoter, the α-factor leader and prochymosin gene. The complete sequence of the BamHI insert is shown in FIG. 6.

To allow selection of yeast transformants, two plasmids, pKS100 and pAB300, were constructed.

pKS100: Plasmid pKS100 was constructed by insertion into pDM100-PC of an 1170 bp HindIII fragment from YEp24 containing the S. cerevisiae URA3 gene.

pAB300: Plasmid pAB300 was constructed by insertion into pDM100-PC of a 3500 bp HindIII-SalI fragment from pGB901 containing the 3' region of the K. lactis LAC4 gene and the G418 resistance marker. The GAPDH/α-factor/prochymosin BamI insert in pDM100-PC is illustrated in FIG. 6.

2. Transformation of K. lactis and S. cerevisiae

Plasmid pKS100 was digested at the BglII site in the prochymosin coding region and used to transform K. lactis strain KRN201-6. This strain is a derivative of strain 2UV21 (a lac4 trp1 ura3 [kil°]) in which the lac4 gene has been replaced by the LAC4 promoter-prochymosin gene fusion from pGB901. Integration of pKS100 is thus targeted to the integrated prochymosin coding region. Plasmid pKS100 was also used to transform S. cerevisiae strain AB110 (α ura3 leu2 his4 pep4-3 [cir°]), in this case targeting to the SacII site in the 3' region of the GAPDH gene.

The resulting transformants were grown to saturation in liquid YEPD medium, and the culture supernatants and cell lysates assayed for chymosin activity after activation at pH 2. As shown by the results summarized in Table 5 below, the K. lactis transformants efficiently secreted prochymosin into the medium, whereas the S. cerevisiae transformants secreted only a small fraction of the prochymosin produced.

TABLE 5

Prochymosin production in K. lactis and S. cerevisiae transformants

| Strain | Chymosin Activity (relative units/ml culture) | |
|---|---|---|
| | Cell Extract | Culture Supernatant |
| AB110 | <0.25 | <1.0 |
| AB110::pKS100 | 15.5 | 2.3 |
| KRN201-6 | <0.25 | <1.0 |
| KRN201-6::pKS100 | 12.0 | 333.0 |

Plasmid pAB300 was used to transform K. lactis strain 2UV21 to G418 resistance, targeting integration to the EcoRV site in the 3' region of the LAC4 gene. These transformants were also found to efficiently secrete prochymosin into the culture medium as shown in Table 6 below.

TABLE 6

Prochymosin secretion from α-factor/prochymosin fusions

| Host Strain | Transforming Plasmid | Secreted Chymosin Activity (relative units/ml culture) |
|---|---|---|
| 2UV21 | — | <2 |
| KRN201-6 | — | <2 |
| KRN201-6 | pKS100 | 385 |
| 2UV21 | pAB300 | 294 |

B. Construction of LAC4 Promoter/α-factor Leader/prochymosin Fusions

In order to produce this fusion, two intermediate plasmids were constructed. Plasmid pDM100-PC was partially digested with PstI, ligated to a SalI-PstI adaptor encoding a portion of the α-factor leader and 26 bp of the region 5' to the LAC4 gene, and then digested with HindIII. A 1500 bp fragment was isolated from this mixture and then cloned into pUC18 digested with HindIII and SalI to produce pKS102.

A synthetic E. coli lac operator was ligated into the SalI site just 5' to the α-factor leader coding sequence in pKS102 to produce the plasmid pKS103. This was done because the LAC4 promoter/α-factor leader/prochymosin fusion may be toxic to E. coli.

Figure 7:
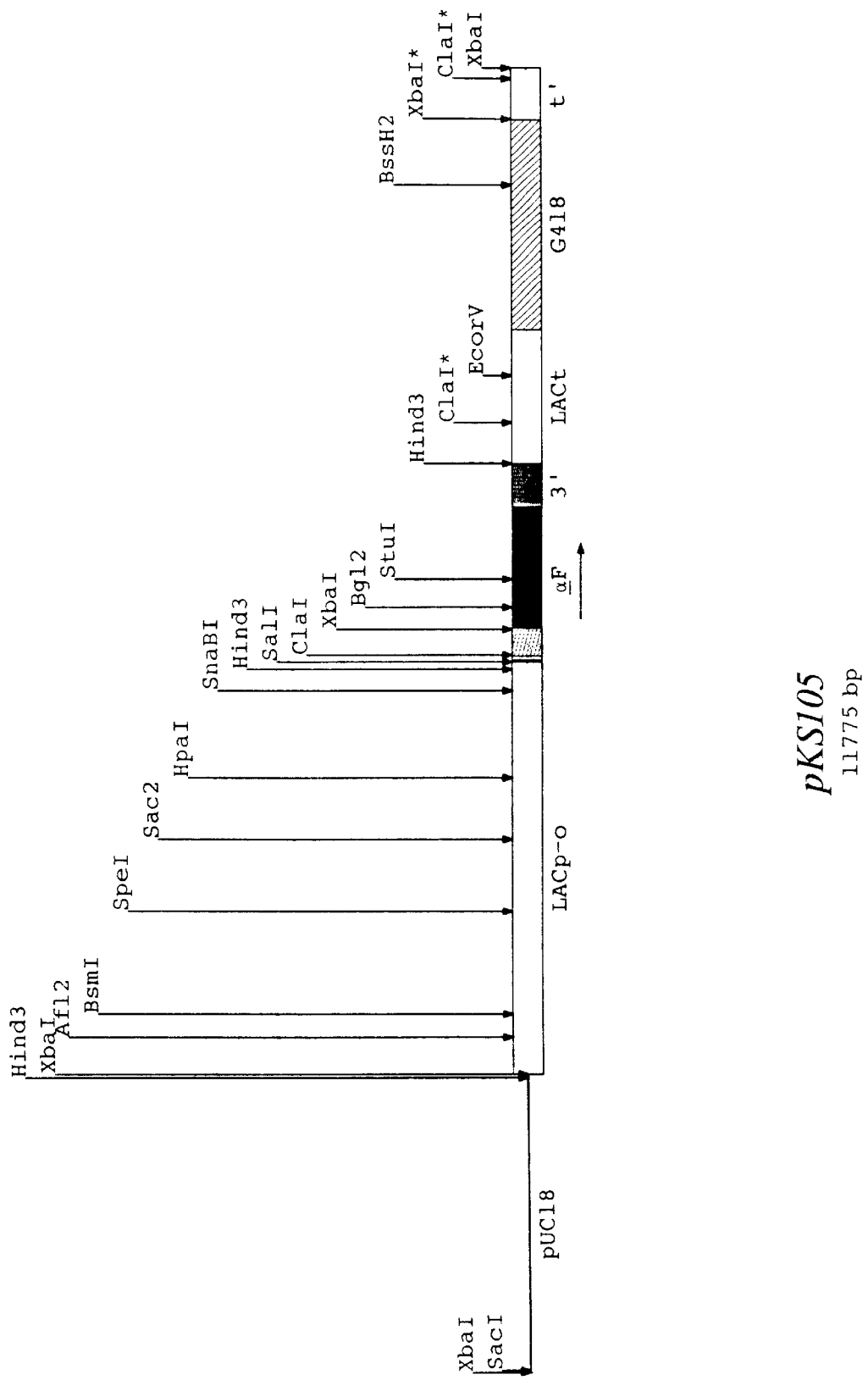
FIG. 7 is a restriction map of plasmid pKS105.

A 490 bp SalI-BglII fragment from pKS103 was isolated and ligated to SalI-BglII-digested pJD15R. Plasmid pJD15R is derived from pGB901 by deletion of the SalI site in the pUC19 polylinker by filling-in to produce pJD15, and then recloning the 8800 bp XbaI fragment in the opposite orientation. From this reaction the plasmid pKS105 was isolated. These plasmids are illustrated in FIG. 7.

Plasmid pKS105 was then used to transform *K. lactis* strain CBS 2360 to G418 resistance, using the SacII site in the LAC4 5' region as a targeting site for the integrative transformation. Chymosin production is expressed in units per ml of cells at $OD_{610}$ of 200, see Table 7 below.

TABLE 7

Secretion of Prochymosin by *K. Lactis* Cells Transformed with pKS105*

| Transformant | Supernatant | Pellet |
|---|---|---|
| 1 | 111 | 3.3 |
| 2 | 147 | 4.5 |
| 3 | 124 | 3.7 |
| 4 | 125 | 3.0 |

*Chymosin activity in relative units/ml culture.

Example 7

Construction of Plasmids Containing the *Kluyveromyces lactis* α-factor Sequence for Efficient Secretion A. Isolation and Use of *K. lactis* α-factor Signal Sequence Biological assays of culture supernatants were carried out as described (Julius et al., Cell (1983) 32:839) using as a tester strain the *S. cerevisiae* Mat a sst2-3 strain RC687. *K. lactis* strain CBS 141(α) was grown in a medium consisting of 0.5% glucose, 0.17% yeast nitrogen base without ammonium sulfate (Difco), and 0.002% ammonium sulfate. After removal of cells by centrifugation, acetic acid was added to the culture supernatant to a concentration of 0.1 M, and the supernatant was passed over a column of Bio-Rex 70 (Biorad). The column was washed with 0.1 M acetic acid and then the α-factor was eluted with 80% ethanol/10 mM HCl. The eluate was evaporated to dryness and then dissolved in 0.1% trifluoroacetic acid (TFA)/20% acetonitrile and applied to a reverse-phase HPLC guard column. The column was washed stepwise with solutions containing 0.1% TFA and 20%, 40%, 60% and 80% acetonitrile. The 60% fraction, containing the α-factor activity, was then applied to an analytical C-18 HPLC column and eluted with a gradient of 20% to 80% acetonitrile in 0.1% TFA. Fractions were collected and assayed for α-factor activity. The fractions containing α-factor activity were dried and subjected to amino acid sequence analysis.

B. Hybridization Screening of Plasmid Libraries

Pools of oligonucleotides were labeled using γ-[$^{32}$P]-ATP and T4 polynucleotide kinase. These oligonucleotide probes were used to probe Southern blots or bacterial colonies at 42° C. in the following hybridization solution: 4×SSC, 50 mM $KH_2PO_4$ pH 7, 1% sarkosyl, 10% dextran sulfate, 200 μg/ml sonicated, denatured salmon sperm DNA. Filters were washed in 2×SSC, 0.1% SDS at 42° C.

A plasmid library in the vector pJS109, containing inserts resulting from a limited Sau3AI digest of genomic DNA from *K. lactis* strain SD11 (a trp1 lac4), size-fractionated to purify fragments >5000 bp was screened with these probes by plating transformants of *E. coli* strain HB101 at a density of 500–2000 colonies per 80 mm plate of L-agar containing 100 μg/ml ampicillin. DNA was transferred from the colonies to nitrocellulose filters and these filters hybridized as described above. Areas on the original plates corresponding to regions of hybridization signals on the filters were picked, then replated and retested by hybridization to isolate single colonies with plasmids containing hybridizing sequences. Positive colonies were further tested by Southern blot analysis of DNA purified from small cultures.

Plasmids purified from hybridization-positive colonies were digested with a variety of restriction enzymes and the resulting fragments analyzed by Southern blot analysis using the same hybridization probes in order to identify restriction fragments of size suitable for DNA sequence analysis. Fragments thus identified were purified by agarose gel electrophoresis and cloned into appropriate MP18 and MP19 vectors. DNA sequence analysis was then performed.

C. Isolation of Kluyveromyces α-factor

The first 10 amino acids of the *K. lactis* α-factor showed a definite homology to that from *S. cerevisiae*, with 6 identical residues. This sequence is shown below:

Trp-Ser-Trp-Ile-Thr-Leu-Arg-Pro-Gly-Gln

This protein sequence was used to design a set of oligonucleotides deduced to be complementary to the structural gene for the corresponding structural gene as shown in FIG. 8. Oligonucleotides including all of the possible codons for a segment of the α-factor peptide were synthesized as two pools of 96 and 48 different molecules.

These two pools were radioactively labeled using γ-[$^{32}$P]-ATP and $T_4$ polynucleotide kinase, and were each used to probe a Southern blot of restriction digests of *K. lactis* DNA. Pool #2 gave strong hybridization to a single fragment and much weaker hybridization to a second fragment in several different digests. Thus, pool 2 was chosen to screen plasmid libraries of *K. lactis* genomic DNA.

Use of these probes to screen plasmid libraries resulted in the isolation of a number of hybridizing clones. DNA sequence analysis of one of these clones, αfk18b, showed it encodes an α-factor related peptide which bears a strong similarity to the precursor of the *S. cerevisiae* α-factor peptide. The hybridizing segment was located on a PstI-EcoRI fragment of about 1000 bp. The sequence of this fragment is shown in FIG. 9. The *K. lactis* precursor contains only 2 sites for the addition of N-linked carbohydrate chains. In addition, the spacers of the *K. lactis* repeats are longer than those of the *S. cerevisiae* repeats and show a more diverse sequence with the pattern X-Ala/Pro rather than the Glu/Ala-Pro sequences found in *S. cerevisiae*. A comparison of the DNA sequences showed a strong degree of homology throughout the coding region.

D. Construction of Plasmids

Figure 10:
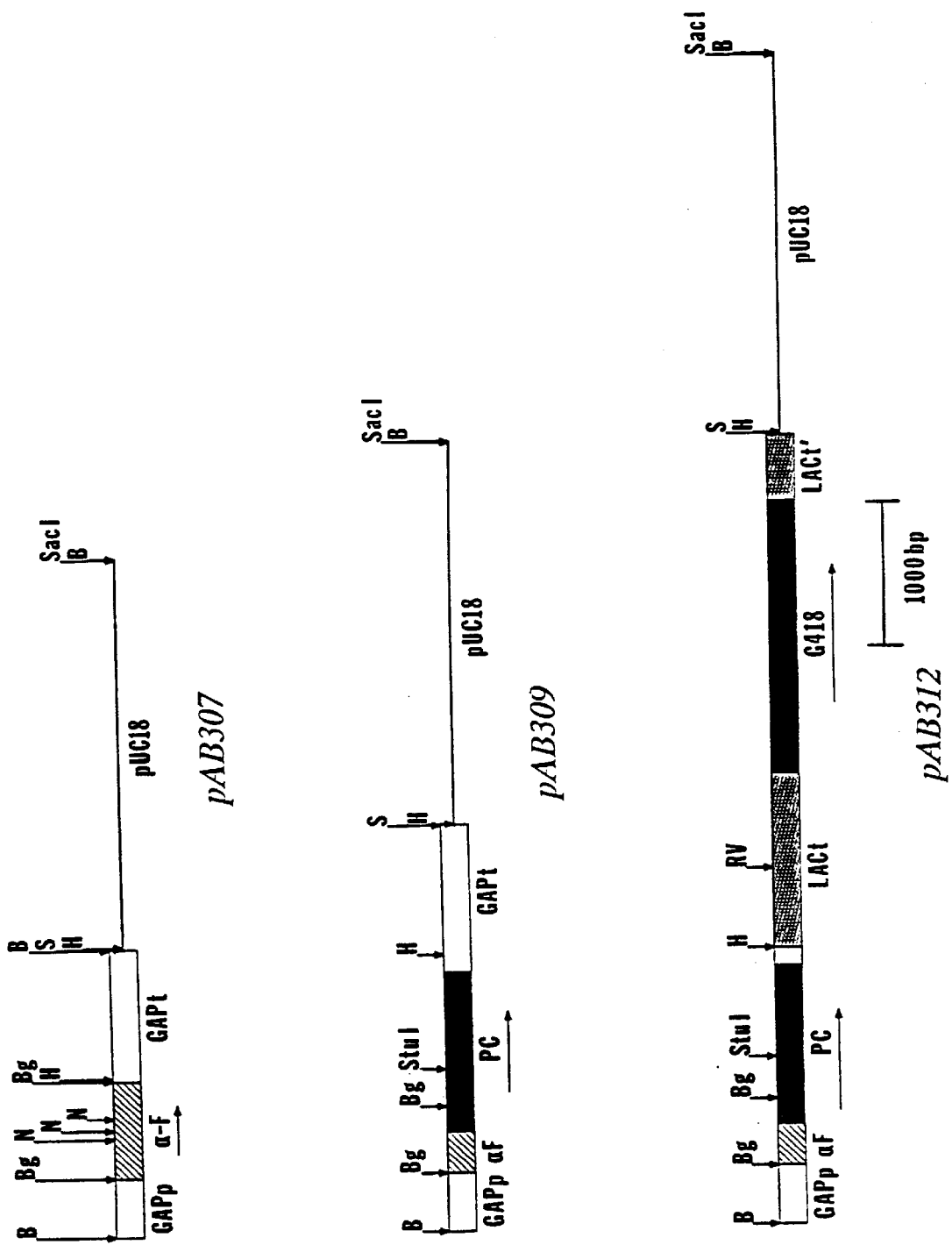
FIG. 10 is a description of plasmids employed for expression of the fusion of the α-factor signal sequence and the prochymosin structural gene.

A series of plasmids (shown in FIG. 10) were constructed in order to provide a fusion of the *K. lactis* α-factor leader to prochymosin expressed under the transcriptional control of a strong promoter.

pAB307: A 673 bp SspI-EcoRI fragment from αfk18b (FIG. 9) was modified by filling the EcoRI overhang by Klenow enzyme and addition of BglII linkers to the blunt ends. This fragment was then inserted into a BglII site joining the promoter and terminator regions of the *S. cerevisiae* glyceraldehyde-3-phosphate dehydrogenase gene (GAPDH). This cassette was cloned as a BamHI fragment in pUC18, resulting in pAB307.

pAB309: Fusion of sequences encoding the α-leader and bovine prochymosin was then performed. First pAB307 was digested with NcoI and the cohesive ends made blunt by treatment with mung bean nuclease. The resulting product was then digested with SalI. To this was ligated a 2000 bp EcoRV-SalI fragment containing sequences encoding prochymosin and the *S. cerevisiae* transcriptional termination region. This fragment was derived from plasmid pJS111 in which a XbaI-BamHI adaptor had been added to the 5' end of a fragment containing prochymosin cDNA fused to the *S. cerevisiae* GAPDH transcriptional termination region. This ligation mixture was used to transform *E. coli* strain HB101 and a transformant carrying the plasmid pAB309 was isolated. The sequences around the junction of this fusion are shown in FIG. 11 and the sequence of the entire BamHI-SalI insert of pAB309 is shown in FIG. 12.

```
KRN-303-1
 1             5              10             15
Glu-Ala-Asp-Ala-Ser-His-His-Met-Ala-Glu-Ile-Thr-Arg-Ile-Pro
``` pAB312: In order to obtain transformation of *K. lactis* strains, a 3560 bp HindIII fragment derived from pGB901 was inserted into pAB309 producing plasmid pAB312. The HindIII fragment contains the 3' region of the *K. lactis* LAC4 gene and a fusion of the *S. cerevisiae* ADH1 promoter to the bacterial G418-resistance structural gene.

pAB313 and pAB314: A 1900 bp SacI-HindIII was isolated from pAB309 and cloned into MP19 (Yanisch-Perron et at., Gene (1985) 33:103). Single-stranded phage DNA was prepared and used as a template for in vitro mutagenesis with one of the two oligonucleotide primers shown in FIG. 13. The M13 phage M19/αk11.5 and MP19/αk12.2 were prepared using Primer #1 and Primer #2, respectively.

Double-stranded RF DNA was prepared from these phages, and 1100 bp SacI-StuI fragments isolated from each. These fragments were ligated to a 7100 bp SacI-StuI fragment from pAB312. The resulting plasmids pAB313 and pAB314 were isolated with the sequence alterations illustrated in FIG. 13.

E. Transformation of Kluyveromyces

Plasmid pAB312 was digested with EcoRV (to target integration to the LAC4 region of the *K. lactis* genome) and was then used to transform *K. lactis* strain 2UV21 (a ura3 trp1 lac4 [kil°]) to G418 resistance. The plasmids pAB313 and pAB314 were used to transform strain 2UV21 to G418 resistance. Cultures of transformants 2UV21::pAB312, 2UV21::pAB313 and 2UV21::pAB314 were grown and culture supernatants assayed for chymosin activity as above.

A number of these transformants, as well. as an untransformed control strain, were grown for 36 hours in 1 ml of medium composed of 1% yeast extract, 2% peptone, 2% glucose, 0.17% yeast nitrogen base, 50 μg/ml tryptophan and 50 μg/ml uracil. Culture supernatants were then assayed for chymosin activity after acid activation. All of the transformants were found to secrete activatable chymosin. The results are shown in the following Table 8.

TABLE 8

Secretion of prochymosin in Kluyveromyces

| Strain | Host | Plasmid | Chymosin Activity (relative units/ml culture) |
|---|---|---|---|
| 2UV21 | 2UV21 | — | <2 |
| KRN303-1 | 2UV21 | pAB312 | 256 |
| KRN304-4 | 2UV21 | pAB313 | 175 |
| KRN305-2 | 2UV21 | pAB314 | 206 |

Each of the transformants was found to secrete a single prochymosin-related species as judged by SDS polyacrylamide gel electrophoresis of trichloroacetic acid-precipitated culture supernatants. The prochymosin-related protein secreted by pAB312 transformants appeared to be of slightly higher molecular weight than those secreted by pAB313 and pAB314 transformants as determined by electrophoretic mobility.

The major species secreted by KRN303-1 and KRN304-4 were purified by preparative SDS polyacrylamide gel electrophoresis and subjected to gas phase amino acid sequence analysis. The N-terminal sequences of these species are given below.

```
KRN304-4
 1             5
Ala-Glu-Ile-Thr-Arg-Ile
```

These results indicate that the prochymosin-related species secreted by KRN303-1 has undergone no processing of the amino-terminal spacer sequence, while the species secreted from KRN304-4 has the authentic mature prochymosin amino terminus.

Example 8

Secretion of t-PA by *Kluyveromyces lactis* Using an Amyloglucosidase Signal Sequence

A. Cloning of Tissue-type Plasminogen Activator cDNA

A cDNA coding for tissue-type plasminogen activator (t-PA) was obtained in a way similar to that described by Pennica et al. (Nature (1983) 301:214). DNA sequence analysis and restriction mapping confirmed the authenicity of the t-PA cDNA. For expression studies the 2.0 kb BglII fragment (see Pennica et al.), comprising almost the complete coding region for the mature protein and the 3' non-coding region, was used.

B. Introduction of the G418 Resistance Marker in pUC19

Figure 14:
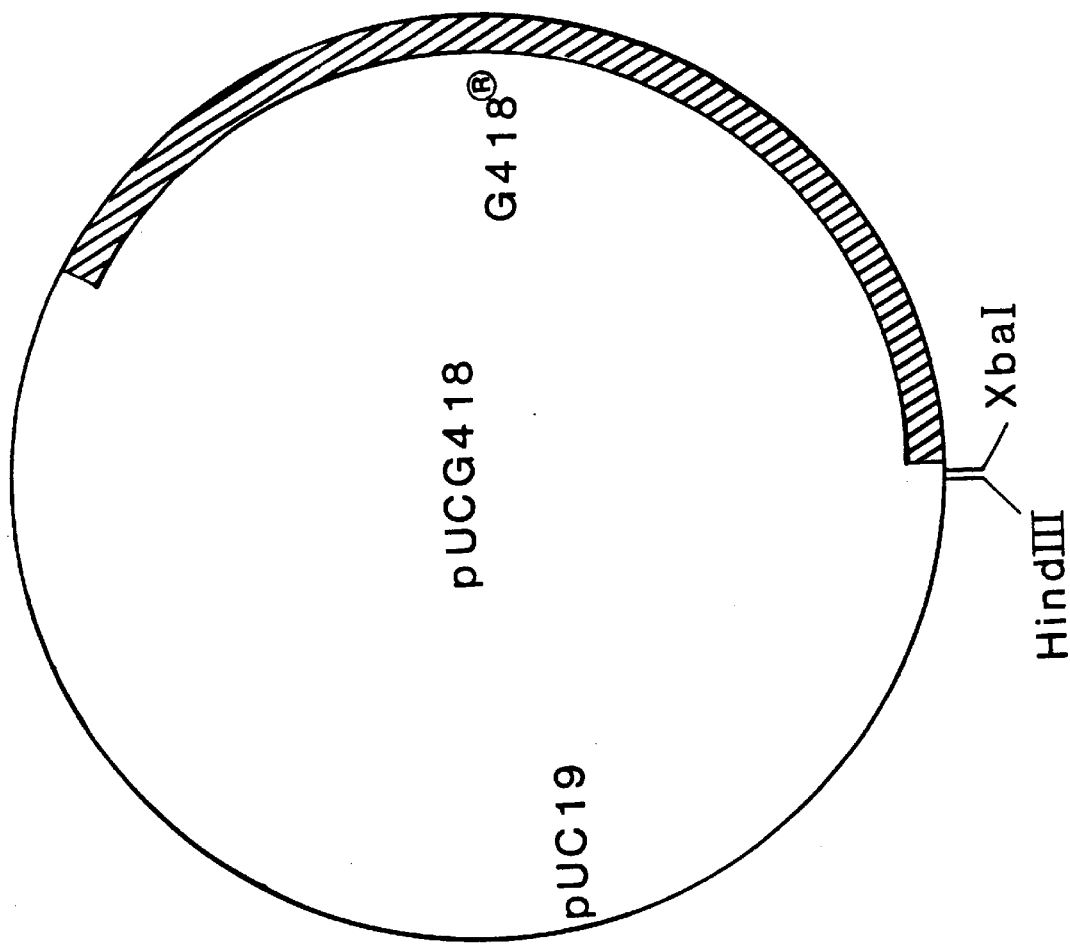
FIG. 14 is a diagram of the plasmid pUCG418.

A DNA fragment comprising the Tn5 gene (Reiss et al., EMBO J. (1984) 3:3317), conferring resistance to G418 under the direction of the alcohol dehydrogenase I (ADHI) promoter from *S. cerevisiae,* similar to that described by Bennetzen and Hall, J. Biol. Chem. (1982) 257:3018, was inserted into the SmaI site of pUC19 (Yanisch-Perron et al., Gene (1985) 33:103). The obtained plasmid, pUCG418, is shown in FIG. 14. *E. coli* containing pUCG418 was deposited at Centraal Bureau voor Schimmelcultures on Dec. 4, 1987 under CBS 872.87.

C. Construction of pGBtPA1

Figure 15:
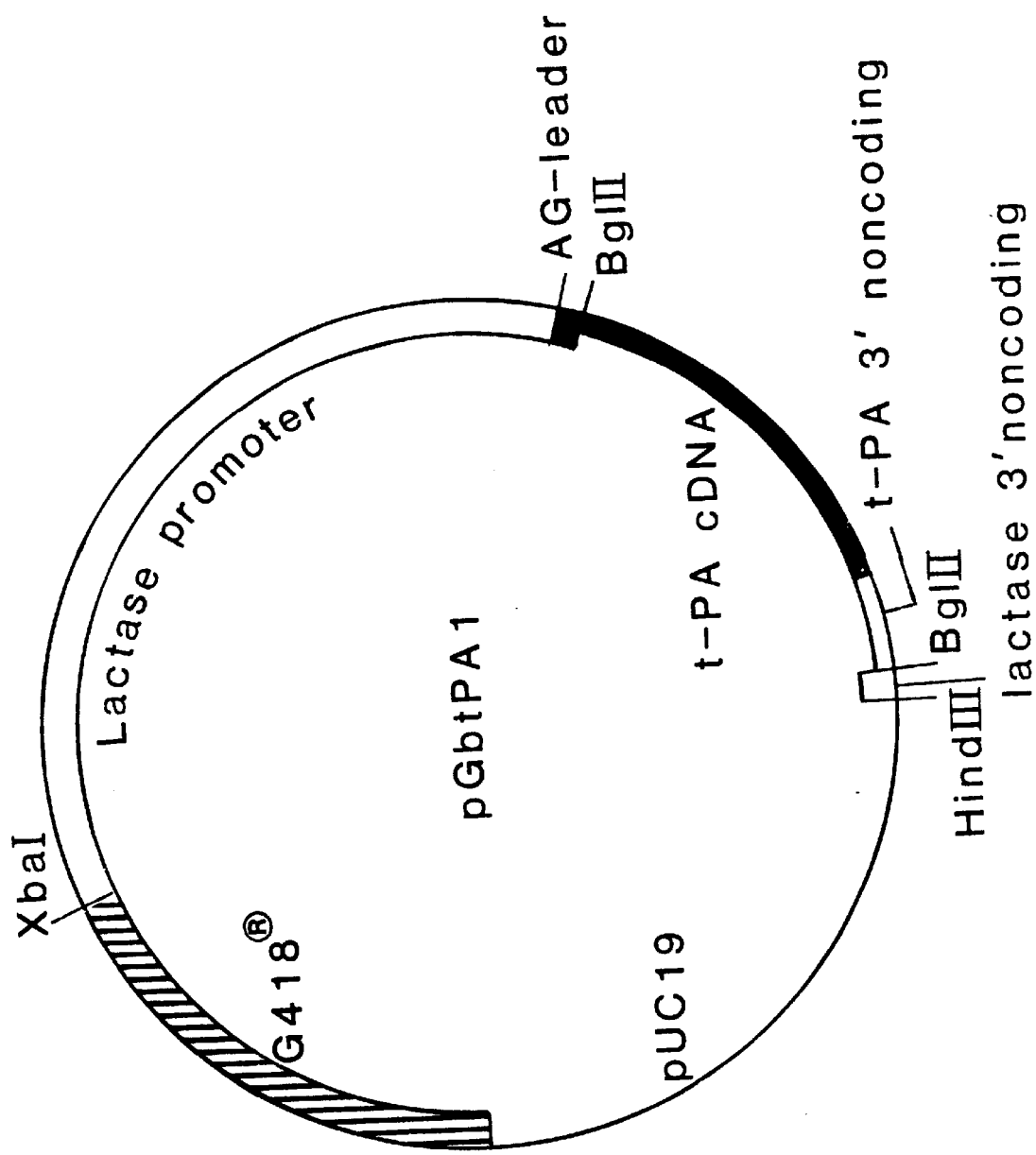
FIG. 15 is a diagram of the plasmid pGBtPA1.

In a few cloning steps pGBtPA1 was constructed (see also FIG. 15 and Table 9) containing the following elements:

(1) pUCG418 (see above) cut with XbaI and HindIII;
(2) the XbaI-SalI fragment from pGB901, containing the lactase promoter;
(3) synthetic DNA coding for the signal sequence of amyloglucosidase from *Aspergillus awamori* (Innis et al., Science (1985) 228:21). The sequence in front of the startcodon was chosen to remove the SalI site at the end of the lactase promoter fragment and further comprises part of the 5' noncoding region of the lactase gene;

(4) the 2.0 kb BalII fragment from the t-PA cDNA (see above);

(5) synthetic DNA, comprising part of the 3' noncoding region of the lactase gene.

TABLE 9

Schematic representation of plasmid pGBtPA1

```
                          XbaI
                           v
..........pUCG418..........TCTAGA.....lactase promoter.....
...........GTCGATCATCGAGAACTGAAAGATATGTCTTGCCTTATGTCTTTCAGA
TCCCTACTAGCTCTATCCGGTCTAGTTTGTACTGGTCTAGCTAACGTTATCTCCAAGAG
 SalI  BglII                               BglII
   v    v                                    v
AGTCGACAGATCT..........t-PA cDNA......AGATCTGATATGAATTTATACT
TAGATAAGTATGTACTTAGATAAGTATGTACTTACAGGTATATTTCTATGAGATACTGA
                       HindIII
                           v
TGTATACATGCATGATAATATTTAAAGCTT
Protein synthesis starts at the underlined ATG codon.
```

D. Transformation of *Kluyveromyces lactis* and Analysis of the Transformants

Transformation of *K. lactis* strain CBS 2360 with pGBtPA1 was performed as described in Example 2. The transformants and the control strain CBS 2360 were grown in YEPD-medium for about 64 hrs. at 30° C. Cells were separated from the culture medium by centrifugation. The cells were resuspended in a physiological salt solution at an $OD_{610}$ of 300 and disrupted by shaking with glass beads for 3 minutes on a Vortex shaker at maximal speed. Cell debris was removed by centrifugation.

A clotlysis assay according to Wallen et al. (Biochim. Biophys. Acta (1982) 719:318) was performed in micro-titer plates. A solution was made, containing 15 mM phosphate buffer (pH 7.3), 0.2 CU/ml plasminogen, 1.5 mg/ml fibrinogen and 0.04% gelatin. Into each well of a microtiter plate 10 μl thrombine (13.9 NIH units/ml), 25 μl sample and 65 μl of the plasminogen/fibrinogen solution were mixed. The reaction was followed by measuring the $OD_{450}$ every 30 min. t-PA from melanoma cells (Kabi Vitrum) was used to provide a calibration curve within every microliter plate.

Table 10 shows the result of a typical analysis of 10 transformants. It is demonstrated that t-PA was found in the culture medium of *K. lactis* transformed with pGBtPA1.

TABLE 10

Clotlysis assay of the cultures from CBS 2360 and from CBS 2360 transformed with pGBtPA1

| transformant | t-PA activity in supernatant |
|---|---|
| 1 | 40 μg/l |
| 2 | 6 μg/l |
| 3 | <3 μg/l |
| 4 | <3 μg/l |
| 5 | 25 μg/l |
| 6 | 3 μg/l |
| 7 | 3 μg/l |
| 8 | <3 μg/l |
| 9 | 3 μg/l |
| 10 | <3 μg/l |
| CBS 2360 1°) | <3 μg/l |
| CBS 2360 2°) | <3 μg/l |
| CBS 2360 3°) | <3 μg/l |
| CBS 2360 4°) | <3 μg/l |
| CBS 2360 5°) | <3 μg/l |

In some of the cell extracts a slight t-PA activity (≦3 μg/l) was found.

Figure 16:
FIG. 16 shows the secretion of human t-PA by K. lactis as analysed on a SDS-polyacrylamide gel overlayered with a plasminogen/fibrin-agarose gel.

Analysis was also performed on SDS-polyacrylamide gels overlayered with a plasminogen/fibrin-agarose gel according to Granelli-Piperno and Reich (J. Exp. Med. (1978) 148:223). 200 μl of the supernatant of a culture of CBS 2360 or CBS 2360 transformed with pGBtPA1 was precipitated with ethanol and resuspended in 20 μl sample buffer (62.5 mM Tris-HCl pH 6.8, 2% sodium dodecylsulphate, 10% glycerol, Bromophenol Blue). The samples were layered on the gels without prior boiling. The results (shown in FIG. 16) demonstrate the secretion of human t-PA by *K. lactis*. Furthermore, it is clear that most of the secreted material is glycosylated.

The secretion of t-PA was also confirmed by using an ELISA with a monoclonal antibody against human t-PA (ESP5 purchased from Biopool) and by a chromogenic activity assay (a commercial test from Kabi Vitrum).

Example 9

Secretion of t-PA by *Kluyveromyces lactis* Using the Signal Sequence from Human Serum Albumin A. Construction of pGBtPA2

Figure 17:
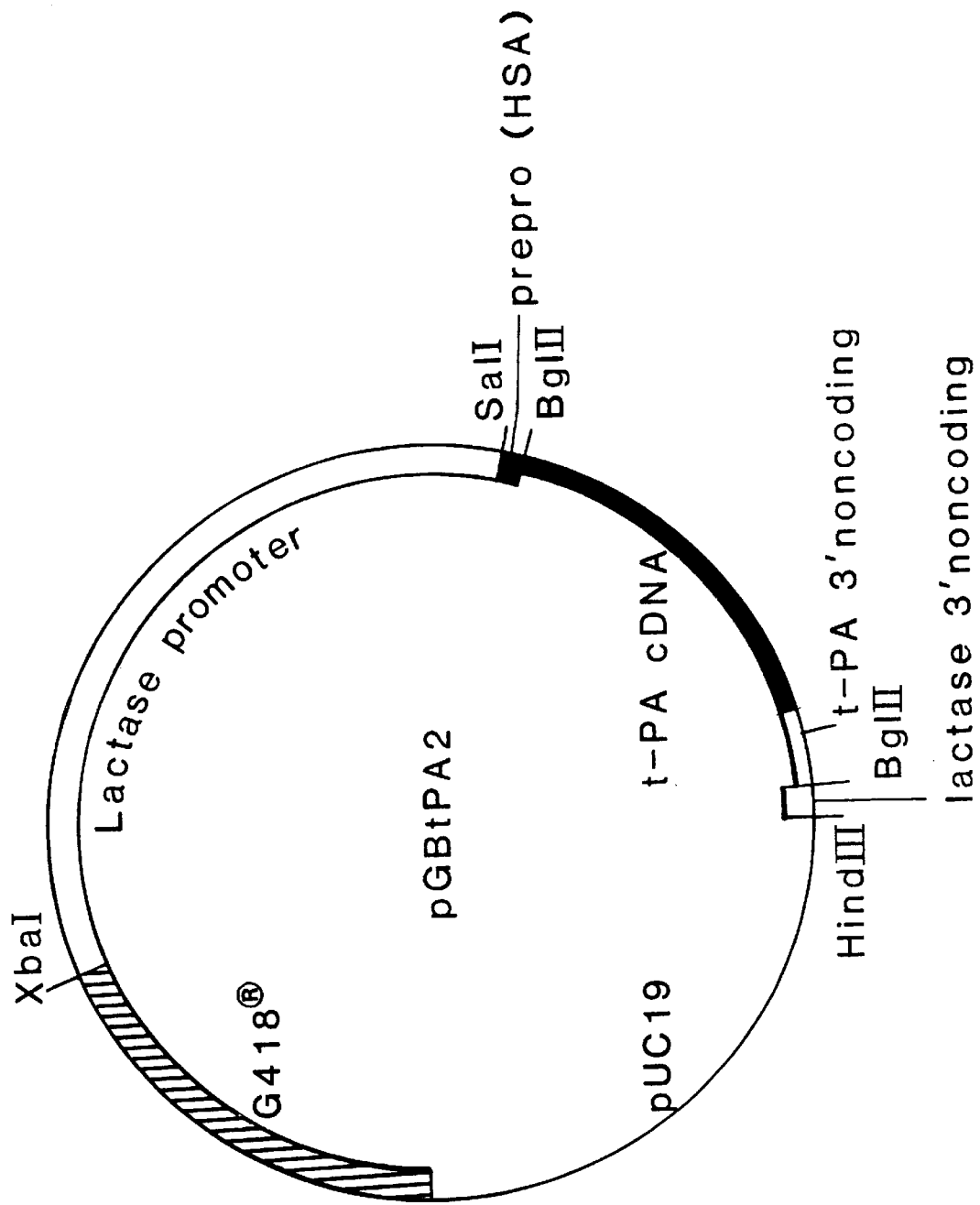
FIG. 17 is a diagram of the plasmid pGBtPA2.

In a few cloning steps pGBtPA2 was constructed (see FIG. 17 and Table 11), containing the following elements:

(1) pUCG418, cut with XbaI and HindIII;

(2) the XbaI-SalI fragment from pGB901, containing the lactase promoter;

(3) synthetic DNA coding for the prepro-region of human serum albumin;

(4) the 2.0 kb BglII fragment from the t-PA cDNA (see Example 8);

(5) synthetic DNA, comprising part of the 3' noncoding region of the lactase gene.

TABLE 11

Schematic representation of plasmid pGBtPA2

```
                                    XbaI
                                     v
..........pUCG418..........TCTAGA........lactase promoter..
          SalI
           v
.............GTCGACAAAAAATGAAGTGGGTTACCTTCATCTCCTTGTTGTTCTT
                                               BglII
                                                 v
GTTCTCCTCCGCTTACTCCAGAGGTGTTTTCAGAAGAGGTGCTAGATCT..........
                                      EcoRV
                            BglII    XhoI
                              v       v     v
t-PA cDNA.....................AGATCTGATATCTCGAGAATTTATACTTA
GATAAGTATGTACTTACAGGTATATTTCTATGAGATACTGATGTATACATGCATGATAA
      HindIII
         v
TATTTAAAGCTT.............
```
Protein synthesis starts at the underlined codon.

B. Transformation of *K. lactis* and Analysis of the Transformants

Transformation of CBS 2360 with pGBtPA2 was performed as described in Example 8. The transformants and the control strain were grown and treated as described in the previous Example. The results of the clotlysis assay are summarized in Table 12.

TABLE 12

Clotlysis assay of the cultures from CBS 2360 and CBS 2360 transformed with pGBtPA2

| transformant | t-PA activity in supernatant |
|---|---|
| 1 | 25 µg/l |
| 2 | 25 µg/l |
| 3 | <3 µg/l |
| 4 | <3 µg/l |
| 5 | 6 µg/l |
| 6 | 12 µg/l |
| 7 | <3 µg/l |
| 8 | <3 µg/l |
| 9 | <3 µg/l |
| 10 | <3 µg/l |
| CBS 2360 1°) | <3 µg/l |
| CBS 2360 2°) | <3 µg/l |
| CBS 2360 3°) | <3 µg/l |
| CBS 2360 4°) | <3 µg/l |
| CBS 2360 5°) | <3 µg/l |

In some of the cell extracts a slight t-PA activity ($\leq 3$ µg/l) was found.

Example 10

Secretion of Human Serum Albumin by *Kluyveromyces lactis*

A. Synthesis and Cloning of the HSA cDNA cDNA encoding human serum albumin was prepared according to the method of Okayama and Berg (Mol. Cell. Biol. (1982) 2:161) using mRNA prepared from human liver. The cDNA was cloned in a vector derived from pBR322 and transformed to *E. coli*. Screening of the transformants was performed using a oligodesoxyribonucleotide based on the sequence of the HSA cDNA clone of Lawn et al., Nucleic Acids Res. (1981) 9:6103). The selected cDNA clone was partially sequenced and compared to the sequence of Lawn et al. This revealed that the first 5 nucleotides of the preproHSA coding region were absent, but the BstEII site at nucleotides 9–15 of the coding region was still found. This BstEII site and the HindIII site in the 3' noncoding region (see Lawn et al., cited above) were used for subcloning in expression vectors.

B. Construction of pGBHSA1

In a few cloning-steps pGBHSA1 was constructed, containing the following elements:
(1) pUCG418 (see Example 8) cut with XbaI and HindIII;
(2) the XbaI-SalI fragment from pGB901 (see Example 1);
(3) synthetic DNA (SalI-HindIII fragment), comprising part of the 3' noncoding region of the lactase gene. The sequence of this fragment is given in Table 13.

TABLE 13

Sequence of the SalI - HindIII fragment of pGBHSA1

```
                           EcoRV
  SalI   NotI    BglII    XhoI
   v      v        v       v    v
  TCGACGCGGCCGCAGATCTGATATCTCGAGAATTTATACTTAGATAAGTATGTACTTACA
      GCGCCGGCGTCTAGACTATAGAGCTCTTAAATATGAATCTATTCATACATGAATGT
                                                     HindIII
                                                        v
  GGTATATTTCTATGAGATACTGATGTATACATGCATGATAATATTTAA
  CCATATAAAGATACTCTATGACTACATATGTACGTACTATTATAAATTTCGA
```

C. Construction of pGBHSA2 pGBHSA1 was cut with SalI and EcoRV and synthetic DNA was inserted:

```
SalI            BstEII      StuI
v               v           v
TCGACAAAAATGAAGTGGGTAACCATCGATAGGCCTACTGGGCTCGAGATC

GTTTTTACTTCACCCATTGGTAGCTATCCGGATGACCCGAGCTCTAG
```

The underlined ATG-codon indicate the initiation codon in the ultimate expression construct (pGBHSA3, see below).

The resulting plasmid was named pGBHSA2.

D. Construction of pGBHSA3

Figure 18:
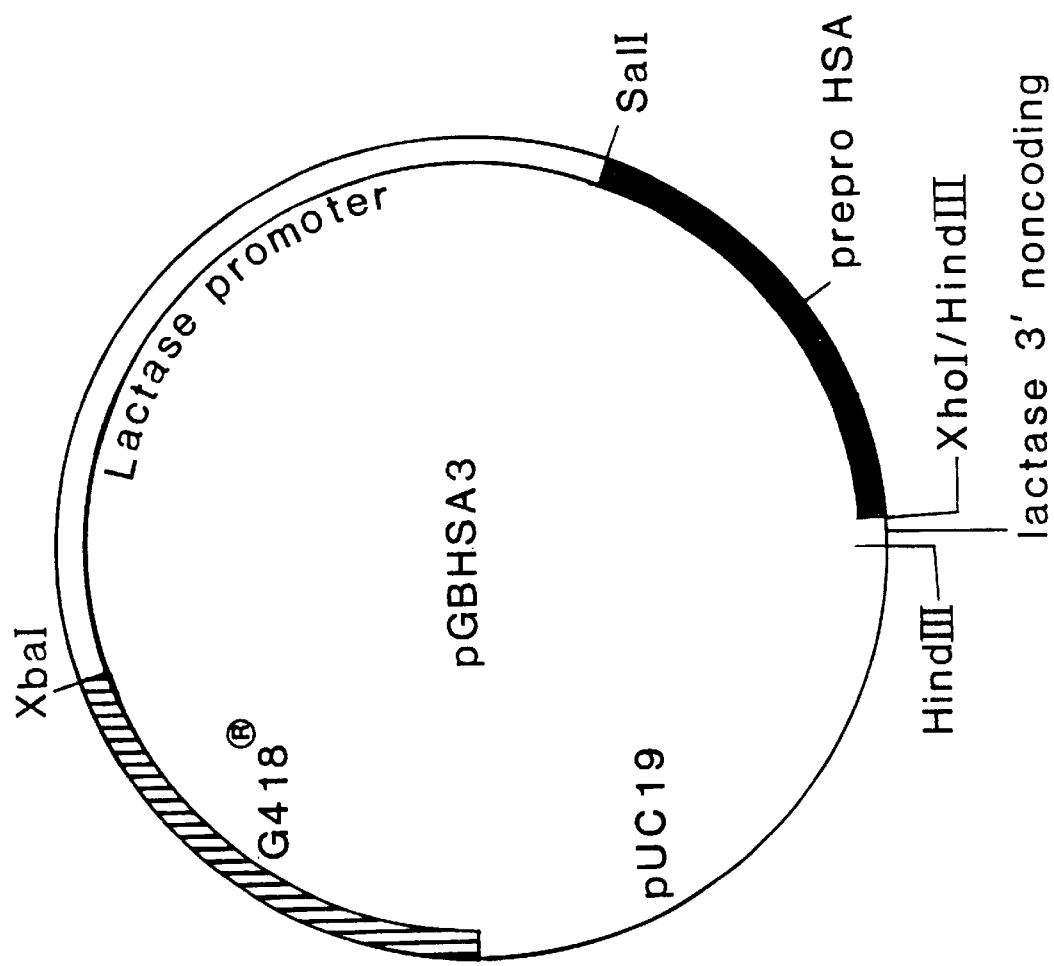
FIG. 18 is a diagram of the plasmid pGBHSA3.

The HSA cDNA-clone was cut with HindIII and the sticky end was filled in, using Klenow DNA polymerase I. Subsequently the DNA was cut with BstEII and the BstEII-HindIII (filled in) fragment, containing almost the complete HSA coding region was purified. pGBHSA2 was digested with XhoI, the sticky ends were filled in using Klenow DNA polymerase I and digestion with BstEII was performed. In the resulting vector the HSA encoding fragment (BstEII-HindIII (filled in)) was inserted. The obtained plasmid, pGBHSA3, is shown in FIG. 18.

Figure 19:
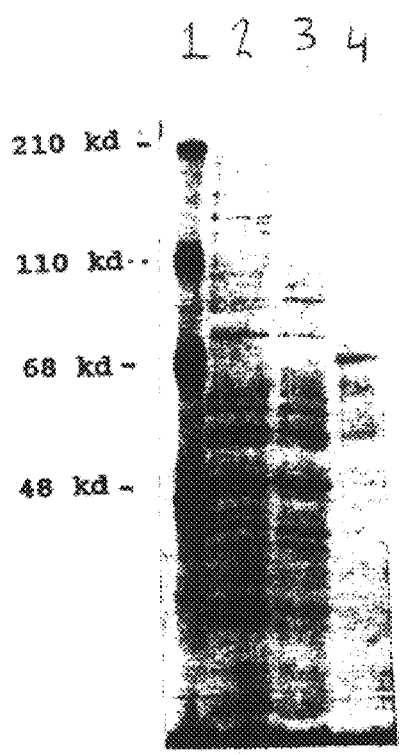
FIG. 19 shows the secretion of HSA by K. lactis as analysed on a 10% polyacrylamide gel.

E. Transformation of *Kluyveromyces lactis* and Analysis of the Transformants Transformation of *K. lactis* strain 2360 with pGBHSA3 was performed as described in Example 2. Transformants and the control strain CBS 2360 were grown in YEPD medium for about 64 hrs at 30° C. The cells were separated from the culture medium by centrifugation. Samples of 30 μl were taken from the supernatants and analysed by electrophoresis on a 10% polyacrylamide gel according to Laemmli (Nature 227, 680 (1970)). The results shown in FIG. 19 demonstrate that HSA is secreted into the culture medium by *K. lactis* cells transformed with pGBHSA3. There is also an indication that the secretion of other proteins is reduced in the HSA producing cells.

The above results demonstrate that one can obtain efficient, convenient expression of exogenous genes in Kluyveromyces strains. Furthermore, the Kluyveromyces strains appear to be particularly useful for providing highly efficient secretion and processing of a wide variety of proteins, as illustrated by the results with prochymosin. Constructs and vectors are provided which allow for the introduction of an exogenous gene under the regulatory control of efficient promoters in Kluyveromyces and, as desired, joining to signal sequences which provide for translocation of the exogenous gene, particularly secretion. Thus, a fermentation system is provided for commercial production of a wide variety of exogenous proteins in an active or activatable form.

The following organisms have been deposited with the American Type Culture Collection on Jun. 30, 1987: 2UV21, ATCC Accession No. 20855; KRN201-6, ATCC Accession No. 20854; HB101 pAB307, ATCC Accession No. 67454; HB101 pAB312, ATCC Accession No. 67455.

Although the foregoing invention has been described in some detail by way of illustration and example for purposes of clarity of understanding, it will be obvious that certain changes and modifications may be practiced within the scope of the appended claims.

What is claimed is:

1. A method for producing a polypeptide of interest in a Kluyveromyces host cell, said method comprising:

growing a Kluyveromyces host cell comprising an expression cassette which comprises as components, in the direction of transcription, a transcriptional regulatory region and translational initiation region functional in said host cell; a DNA sequence which encodes said polypeptide of interest; and translational and transcriptional termination regions functional in said host cell, wherein expression of said DNA sequence is under regulatory control of said transcriptional and translational regions and wherein said components are operably linked so as to provide for expression of said DNA sequence, whereby said polypeptide of interest is expressed in and secreted by said host cell.

2. The method according to claim 1, wherein said polypeptide of interest is isolated from the culture medium.

3. The method according to claim 1, wherein said polypeptide of interest is an enzyme.

4. The method according to claim 1, wherein said polypeptide of interest is human serum albumin.

5. The method according to claim 1, wherein said host cell is an industrial strain of Kluyveromyces.

6. The method according to claim 1, wherein said host cell is *K. lactis* or *K. fragilis*.

7. The method according to claim 6, wherein said expression cassette is integrated into the chromosome of said host cell.

\* \* \* \* \*